United States Patent
Svetlov et al.

(10) Patent No.: US 10,646,555 B2
(45) Date of Patent: May 12, 2020

(54) COMPOSITIONS AND METHODS RELATING TO ARGININOSUCCINATE SYNTHETASE

(71) Applicant: BANYAN BIOMARKERS, INC., Alachua, FL (US)

(72) Inventors: Stanislav I. Svetlov, Alachua, FL (US); Victor Prima, Alachua, FL (US); Alvin Wang, Alachua, FL (US); Gabriel Molina, Alachua, FL (US); Kevin Ka-wang Wang, Gainesville, FL (US)

(73) Assignee: BioRegency, Inc., San Diego, CA (US)

( * ) Notice: Subject to any disclaimer, the term of this patent is extended or adjusted under 35 U.S.C. 154(b) by 0 days.

(21) Appl. No.: 15/625,497

(22) Filed: Jun. 16, 2017

(65) Prior Publication Data

US 2017/0281738 A1  Oct. 5, 2017

Related U.S. Application Data

(62) Division of application No. 14/116,817, filed as application No. PCT/US2011/022561 on Jan. 26, 2011, now Pat. No. 9,682,132.

(60) Provisional application No. 61/298,309, filed on Jan. 26, 2010.

(51) Int. Cl.
| | |
|---|---|
| G01N 33/573 | (2006.01) |
| A61K 38/53 | (2006.01) |
| A61K 38/45 | (2006.01) |
| C12Q 1/25 | (2006.01) |

(52) U.S. Cl.
CPC .............. *A61K 38/53* (2013.01); *A61K 38/45* (2013.01); *C12Q 1/25* (2013.01); *C12Y 603/04005* (2013.01); *G01N 33/573* (2013.01); *G01N 2333/9015* (2013.01); *G01N 2800/26* (2013.01); *G01N 2800/42* (2013.01)

(58) Field of Classification Search
CPC ... A61K 38/53; A61K 38/45; A61K 47/48215
See application file for complete search history.

(56) References Cited

U.S. PATENT DOCUMENTS

| | | | |
|---|---|---|---|
| 4,366,241 A | 12/1982 | Tom et al. | |
| 4,376,110 A | 3/1983 | David et al. | |
| 4,517,288 A | 5/1985 | Giegel et al. | |
| 4,702,909 A | 10/1987 | Villarejos et al. | |
| 4,837,168 A | 6/1989 | de Jaeger et al. | |
| 5,045,694 A | 9/1991 | Beavis et al. | |
| 5,118,937 A | 6/1992 | Hillenkamp et al. | |
| 5,545,625 A | 8/1996 | Gross et al. | |
| 5,710,132 A | 1/1998 | Moller et al. | |
| 5,719,060 A | 2/1998 | Hutchens et al. | |
| 5,792,664 A | 8/1998 | Chait et al. | |
| 6,136,345 A | 10/2000 | Grimmett et al. | |
| 6,183,977 B1 | 2/2001 | Doyle et al. | |
| 6,225,047 B1 | 5/2001 | Hutchens et al. | |
| 7,645,584 B2 | 1/2010 | Svetlov et al. | |
| 8,048,638 B2* | 11/2011 | Svetlov ................... | C12Q 1/00 435/7.1 |
| 2005/0063942 A1 | 3/2005 | Clark et al. | |
| 2005/0136489 A1 | 6/2005 | Tseng et al. | |
| 2005/0260697 A1 | 11/2005 | Wang et al. | |
| 2007/0003982 A1 | 1/2007 | Hayes et al. | |
| 2007/0027634 A1 | 2/2007 | Mendrick et al. | |
| 2009/0047500 A1 | 2/2009 | Maeda | |
| 2010/0196942 A1* | 8/2010 | Svetlov ................... | C12Q 1/00 435/25 |
| 2010/0247508 A1 | 9/2010 | Leung et al. | |
| 2010/0247580 A1 | 9/2010 | Coche et al. | |

FOREIGN PATENT DOCUMENTS

| | | |
|---|---|---|
| JP | H10512142 A | 11/1998 |
| JP | 2000505544 A | 5/2000 |
| JP | 2000514309 A | 10/2000 |
| JP | 2005328714 A | 12/2005 |
| JP | 2005538380 A | 12/2005 |
| JP | 2007532915 A | 11/2007 |
| JP | 2007535318 A | 12/2007 |
| JP | 2010019864 A | 1/2010 |
| WO | 9324834 A1 | 12/1993 |
| WO | 9951773 A1 | 10/1999 |
| WO | 0004389 A2 | 1/2000 |
| WO | 0056934 A1 | 9/2000 |
| WO | 2003085083 A2 | 10/2003 |
| WO | 2009100131 A2 | 8/2009 |

(Continued)

OTHER PUBLICATIONS

Kohler, G. and Milstein, C., "Continuous Cultures of Fused Cells Secreting Antibody of Predefined Specificity", Nature, Aug. 7, 1975, pp. 495-497, vol. 256, issue 5517, The Journal of Immunology (2005), reprinted with permission; Macmillan Publishers, Ltd. (1975).

O'Brien, William E., "A Continuous Spectrophotometric Assay for Argininosuccinate Synthetase Based on Pyrophosphate Formation", Analytical Biochemistry, Aug. 3, 1976, pp. 423-430, vol. 76, issue 2, Academic Press, Inc. (1976).

Kimball, Margaret E. and Jacoby, Lee B., "Purification and Properties of Argininosuccinate Synthetase from Normal and Canavanine-Resistant Human Lymphoblasts", Biochemistry (1980), pp. 705-709, vol. 19.

Miura, Toshiaki, Kashiwamura, Megumi, and Kimura, Michiya, "Enzymatic Method for the Assay of Serum Argininosuccinate Lyase", Analytical Biochemistry (1987), pp. 482-487, vol. 164, issue 2, Academic Press, Inc. (1987).

(Continued)

*Primary Examiner* — Maryam Monshipouri
(74) *Attorney, Agent, or Firm* — Avery N. Goldstein; Blue Filament Law PLLC

(57) ABSTRACT

Processes and compositions for the therapeutic treatment of pathogenic Gram-negative bacterial infection are provided whereby argininosuccinate synthetase or PEGylated argininosuccinate synthetase is administered to a subject to inactivate endotoxin thereby reducing the likelihood of bacterial sepsis and improving patient outcome.

12 Claims, 12 Drawing Sheets

Specification includes a Sequence Listing.

(56) References Cited

FOREIGN PATENT DOCUMENTS

| WO | 2009146915 A2 | 12/2009 |
| WO | 2010005133 A1 | 1/2010 |
| WO | 2010019553 A2 | 2/2010 |
| WO | 2010148391 A2 | 12/2010 |

OTHER PUBLICATIONS

Lazar, Eliane, Watanabe, Shinichi, Dalton, Stephen, and Sporn, Michael B., "Transforming Growth Factor α: Mutation of Aspartic Acid 47 and Leucine 48 Results in Different Biological Activities", Molecular and Cellular Biology, Mar. 1988, pp. 1247-1252, vol. 8, issue 3, American Society for Microbiology (1988).

Ward, E. Sally et al., "Binding Activities of a Repertoire of Single Immunoglobulin Variable Domains Secreted from *Escherichia coli*", Nature, Oct. 12, 1989, pp. 544-546, vol. 341, issue 12, Nature Publishing Group (1989).

Hill, Margaret A. and Preiss, Jack, "Functional Analysis of Conserved Histidines in ADP-Glucose Pyrophosphorylase from *Escherichia coli*", Biochemical and Biophysical Research Communications (1998), pp. 573-577, vol. 244, issue 2, Article No. RC988301, Academic Press (1998).

Wacey, A.I. et al., "Disentangling the Perturbational Effects of Amino Acid Substitutions in the DNA-Binding Domain of p53", Human Genetics (1999), pp. 15-22, vol. 104, Springer-Verlag (1999).

Tabuchi, Shoko et al., "Regulation of Genes for Inducible Nitric Oxide Synthase and Urea Cycle Enzymes in Rat Liver in Endotoxin Shock", Biochemical and Biophysical Research Communications (2000), pp. 221-224, vol. 268, Academic Press (2000).

Roberts, M.J., Bentley, M.D., and Harris, J.M., "Chemistry for Peptide and Protein PEGylation", Advanced Drug Delivery Reviews (2012), pp. 116-127, vol. 64, Elsevier B.V. (2002).

Holtsberg, Frederick W., "Poly(ethylene glycol) (PEG) Conjugated Arginine Deiminase: Effects of PEG Formulations on its Pharmacological Properties", Journal of Controlled Release (2002), pp. 259-271, vol. 80, issue 1/3, Elsevier Science B.V. (2002).

Kim, Won et al., "Comparison of Proteome Between Hepatitis B Virus- and Hepatitis C Virus-Associated Hepatocellular Carcinoma", Clinical Cancer Research, Nov. 15, 2003, pp. 5493-5500, vol. 9, American Association for Cancer Research (2003).

Guo, Haiwei H., Choe, Juno, and Loeb, Lawrence A., "Protein Tolerance to Random Amino Acid Change", PNAS, Jun. 22, 2004, pp. 9205-9210, vol. 101, issue 25.

Satoh, Motonobu et al., "Liver Argininosuccinate Synthetase Binds to Bacterial Lipopolysaccharides and Lipid A and Inactivates their Biological Activities", Journal of Endotoxin Research, pp. 21-38, vol. 12, issue 1, W.S. Maney & Son Ltd. (2006).

Svetlov, S.I. et al., "Identification and Preliminary Validation of Novel Biomarkers of Acute Hepatic Ischaemia/reperfusion Injury Using Dual-platform Proteomic/degradomic Approaches", Biomarkers, Jul.-Aug. 2006, pp. 355-369, vol. 11, issue 4, Informa Healthcare (2006).

Satoh, Motonobu et al, "Clearance of Bacterial Lipopolysaccharides and Lipid A by the Liver and the Role of Argininosuccinate Synthetase", Innate Immunity (2008), pp. 51-60, vol. 14, issue 1, SAGE Publications (2008).

New-zealand-white-rabbit (last viewed on Jul. 27, 2016); http://wwww.crossroadsrabbitry.com/about-new-zealand-white-rabbits/.

Myers, Eugene W. and Miller, Webb, "Optimal Alignments in Linear Space", CABIOS (1988), pp. 11-17, vol. 4, issue 1, IRL Press Limited, Oxford, England (1988).

Karlin, Samuel and Altschul, Stephen F., "Methods for Assessing the Statistical Significance of Molecular Sequence Features by Using General Scoring Schemes", Proc. Natl. Acad. Sci. USA, Mar. 1990, pp. 2264-2268, vol. 87.

Altschul, Stephen F. et al., "Basic Local Alignment Search Tool", J. Mol. Biol. (1990), pp. 403-410, vol. 215, Academic Press Limited (1990).

Karlin, Samuel and Altschul, Stephen F., "Applications and Statistics for Multiple High-Scoring Segments in Molecular Sequences", Proc. Natl. Acad. Sci. USA, Jun. 1993, pp. 5873-5877, vol. 90.

Yu, Yingjie et al., "Preparation of Recombinant Argininosuccinate Synthetase and Argininosuccinate Lyase: Expression of the Enzymes in Rat Tissues", J. Biochem (1995), pp. 952-957, vol. 117, issue 5.

Altschul, Stephen F. et al, "Gapped BLAST and PSI-BLAST: A New Generation of Protein Database Search Programs", Nucleic Acids Research (1997), pp. 3389-3402, vol. 25, issue 17, Oxford University Press (1997).

Sato, H., "Enzymatic procedure for site-specific pegylation of proteins", Advanced Drug Delivery Reviews, Jun. 17, 2002, pp. 487-504, vol. 54, issue 4, Copyright Elsevier Science B.V. (2002).

Harris, J. Milton and Chess, Robert B., "Effect of pegylation on pharmaceuticals", Nature Reviews Drug Discovery, Mar. 2003, vol. 2, issue 3, pp. 214-221, Copyright Nature Publishing Group (2003).

Moghimi, S. Moein, Hunter, A. Christy, and Murray, J. Clifford, "Nanomedicine: Current Status and Future Prospects", The FASEB Journal, Mar. 2005, pp. 311-330, vol. 19.

Veronese, Francesco M. et al., "Site-Specific Pegylation of G-CSF by Reversible Denaturation", Bioconjugate Chem. (2007), pp. 1824-1830, vol. 18, American Chemical Society (2007); Published on the Web Oct. 18, 2007.

Jevsevar, Simona, Kunstelj, Menci, and Porekar, Vladka Gaberc, "PEGylation of Therapeutic Proteins", Biotechnol. J. (2010), pp. 113-128, vol. 5, Wiley-VCH Verlag GmbH & Co. KGaA, Weinheim (2010).

Prima, Victor et al., "Inhibition of LPS Toxicity by Hepatic Argininosuccinate Synthase (ASS): Novel Roles for ASS in Innate Immune Responses to Bacterial Infection", International Immunopharmacology (2011), pp. 1180-1188, vol. 11, Elsevier B.V. (2011).

International Search Report dated Nov. 23, 2012 for International Application No. PCT/US2011/022561 filed Jan. 26, 2011.

Extended European Search Report dated May 9, 2016 for European Application No. 11859017.3 filed Jan. 26, 2011.

Saheki, T. et al, "Clearance of Argininosuccinate Synthetase from the Circulation in Acute Liver Disease", Clinical Biochemistry, Apr. 1990, pp. 139-141, vol. 23, © 1990 The Canadian Society of Clinical Chemists.

\* cited by examiner

COMPOSITIONS AND METHODS RELATING TO ARGININOSUCCINATE SYNTHETASE

CROSS REFERENCE TO RELATED APPLICATIONS

This application is a divisional application of U.S. Utility application Ser. No. 14/116,817 filed Nov. 11, 2013 that in turn is a US National Phase Application of PCT Application PCT/US2011/022561 filed Jan. 26, 2011 that in turn claims priority to U.S. Provisional Application No. 61/298,309 filed Jan. 26, 2010, the entire contents of which are incorporated herein by reference.

FIELD OF THE INVENTION

The invention relates generally to compositions and methods for detection and treatment of microbial infection in a subject. In specific embodiments, the present invention relates to compositions and methods for detection and treatment of exposure to bacterial endotoxin in a subject.

BACKGROUND OF THE INVENTION

Infection by Gram-negative pathogens is associated with particularly severe pathology, such as sepsis and endotoxic shock. Despite the advances in understanding of pathophysiology of endotoxic shock and sepsis, therapies remain largely symptomatic and supportive.

Sepsis is generally characterized by multi-organ failure including kidney, liver, heart and brain due to bacterial toxins absorbed from infected wounds and circulating in blood. Due to the spread of resistance against conventional antimicrobials in last decade, new agents and new compositions and methods are needed to counter septic challenges. Methods and compositions for detection of bacterial endotoxin exposure in a subject are required for timely and appropriate therapeutic intervention.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

Processes of treating exposure of a subject to a bacterial endotoxin are provided including administering a therapeutically effective amount of argininosuccinate synthetase to a subject in need thereof.

An argininosuccinate synthetase as used in the inventions is optionally recombinantly expressed. In some embodiments, the argininosuccinate synthetase has an amino acid sequence of SEQ ID NO: 1, or a variant thereof, optionally being a truncated human argininosuccinate synthetase. Truncated argininosuccinate synthetase optionally retains an LPS binding site.

In some embodiments, argininosuccinate synthetase is PEGylated. A PEGylated argininosuccinate synthetase is optionally PEGylated with a PEG comprising $PEG_{12}$. PEGylated argininosuccinate synthetase is optionally PEGylated with an unbranched PEG, a branched PEG, or combinations thereof. Several ratios of argininosuccinate synthetase to PEG are operable. In some embodiments the argininosuccinate synthetase and PEG are present in a ratio ranging from 1:1 to 1:400, respectively. PEGylation of argininosuccinate synthetase is optionally random or site-directed. Site-directed PEGylation is optionally directed to argininosuccinate synthetase lysines, histidines, cysteines, or combinations thereof. Optionally, PEGylation includes at least one molecule of $PEG_{12}$, optionally exclusively $PEG_{12}$. Optionally, PEG molecules are associated with argininosuccinate synthetase by a covalent amide bond. PEG molecules attached to argininosuccinate are optionally linear, branched, or a combination thereof.

A subject in the inventive processes is optionally a human. In some embodiments, a subject is infected with one or more Gram-negative bacteria such that the infection produces a subject in need of therapy.

Also provided are processes of detecting exposure to bacterial endotoxin by a subject that includes obtaining a sample from a subject exposed to a bacterial endotoxin prior to obtaining the sample, and determining the presence, level, or activity of argininosuccinate synthetase in the sample from the subject. A sample is optionally blood or a fraction of blood, optionally serum.

DETAILED DESCRIPTION OF EMBODIMENTS OF THE INVENTION

Figure 1:
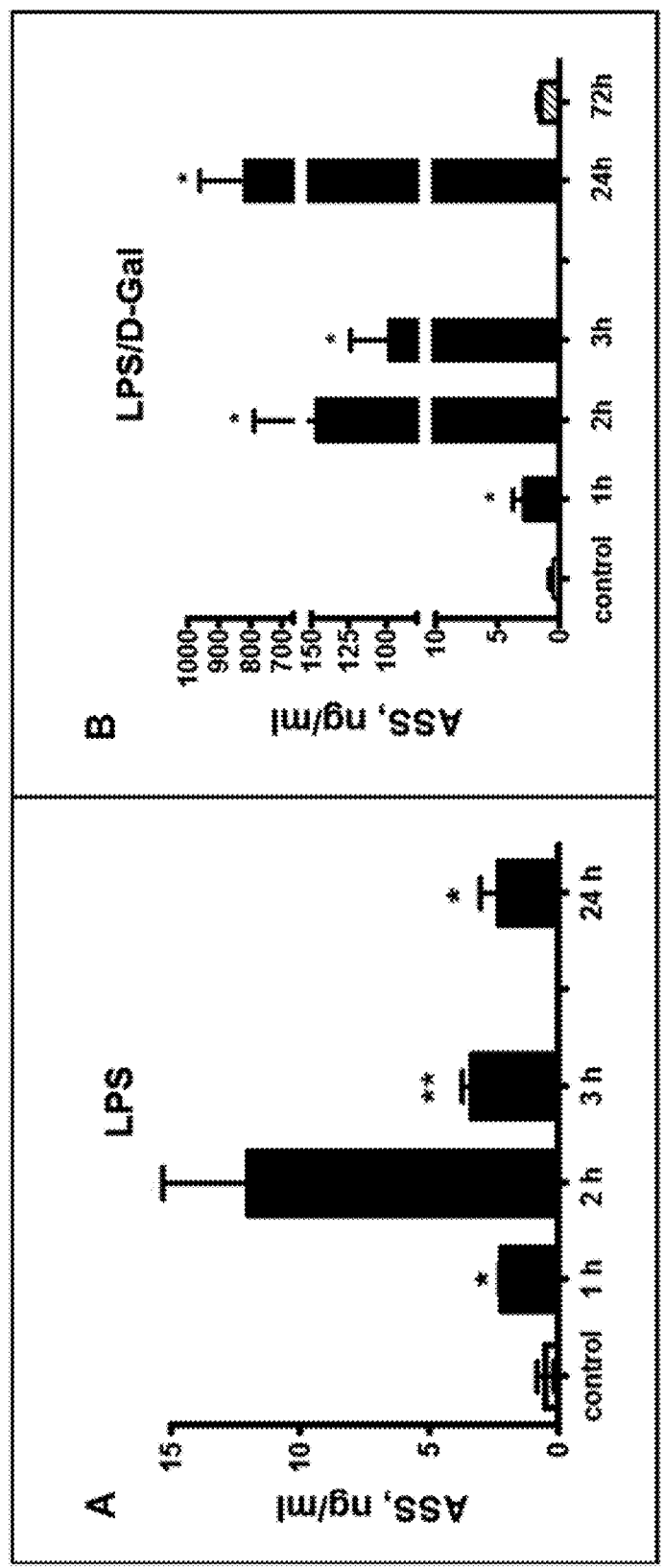
FIG. 1 illustrates increases in endogenous argininosuccinate synthetase in serum from subjects challenged with either LPS alone or along with the liver injury priming agent D-galactosamine.

The following description of particular embodiment(s) of the invention is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only.

Compositions and methods are provided for detection and treatment of bacterial endotoxin exposure in a subject. As such, the invention has utility for detecting the presence of endotoxin in a sample or an organism and for the treatment of infection by Gram-negative bacteria.

The terms "bacterial endotoxin," "lipopolysaccharide" and "LPS" are used interchangeably herein to refer to this well-known structural component of the outer membrane of Gram-negative bacteria that is referred to interchangeably in the art.

Exposure of a subject to bacterial endotoxin occurs most commonly when the subject is infected by Gram-negative bacteria. Illustrative examples of Gram-negative bacteria illustratively include *Escherichia coli, Salmonella, Shigella, Pseudomonas, Neisseria, Haemophilus influenzae, Bordetella pertussis* and *Vibrio cholerae.*

Methods of treating effects of exposure to bacterial endotoxin are provided according to embodiments of the present invention which includes administering argininosuccinate synthetase, or alternatively known as argininosuccinate synthase (ASS) to a subject having, suspected of having, or at risk for, infection by endotoxin-containing bacteria and/or exposure to material suspected of containing bacterial endotoxin.

The terms "argininosuccinate synthetase" and "ASS" are used interchangeably herein to refer to the enzyme argininosuccinate synthetase, optionally human derived, optionally identified herein as SEQ ID NO: 1, or variants thereof.

In addition to the argininosuccinate synthetase protein of SEQ ID NO: 1, the term argininosuccinate synthetase" encompasses variants of SEQ ID NO.1 which may be included in compositions and methods of the present invention. As used herein, the term "variant" refers to naturally occurring genetic variations of the SEQ ID NO.1 and recombinantly prepared variations of SEQ ID NO.1, each of which contain one or more changes in its amino acid sequence compared to SEQ ID NO.1. Such changes include those in which one or more amino acid residues have been modified by amino acid substitution, addition, or deletion. The term "variant" encompasses orthologs of human argininosuccinate synthetase, including, for example, mammalian and bird argininosuccinate synthetase, particularly argininosuccinate synthetase orthologs from non-human primates, cats, dogs, cows, horses, rodents, pigs, sheep, goats, fish and poultry.

Variants are argininosuccinate synthase optionally have at least 85%, 86%, 87%, 88%, 89%, 90%, 91%, 92%, 93%, 94%, 95%, 96%, 97%, 98% or 99% identity to SEQ ID NO: 1.

Mutations can be introduced using standard molecular biology techniques, such as site-directed mutagenesis and PCR-mediated mutagenesis. One of skill in the art will recognize that one or more amino acid mutations can be introduced without altering the functional properties of the argininosuccinate synthetase protein of SEQ ID NO: 1. For example, one or more amino acid substitutions, additions, or deletions can be made without altering the functional properties of the argininosuccinate synthetase protein of SEQ ID NO: 1.

Conservative amino acid substitutions can be made in argininosuccinate synthetase protein of SEQ ID NO: 1 to produce argininosuccinate synthetase protein variants. Conservative amino acid substitutions are art recognized substitutions of one amino acid for another amino acid having similar characteristics. For example, each amino acid may be described as having one or more of the following characteristics: electropositive, electronegative, aliphatic, aromatic, polar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine and valine; aromatic amino acids include phenylalanine, glycine, tyrosine and tryptophan; polar amino acids include aspartate, glutamate, histidine, lysine, asparagine, glutamine, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group. Amino acids may also be described in terms of relative size, alanine, cysteine, aspartate, glycine, asparagine, proline, threonine, serine, valine, all typically considered to be small.

Argininosuccinate synthetase variants can include synthetic amino acid analogs, amino acid derivatives and/or non-standard amino acids, illustratively including, without limitation, alpha-aminobutyric acid, citrulline, canavanine, cyanoalanine, diaminobutyric acid, diaminopimelic acid, dihydroxy-phenylalanine, djenkolic acid, homoarginine, hydroxyproline, norleucine, norvaline, 3-phosphoserine, homoserine, 5-hydroxytryptophan, 1-methylhistidine, 3-methylhistidine, and ornithine.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can also be accomplished using a mathematical algorithm. A preferred, non limiting example of a mathematical algorithm utilized for the comparison of two sequences is the algorithm of Karlin and Altschul, 1990, PNAS 87:2264 2268, modified as in Karlin and Altschul, 1993, PNAS. 90:5873 5877. Such an algorithm is incorporated into the NBLAST and XBLAST programs of Altschul et al., 1990, J. Mol. Biol. 215:403. BLAST nucleotide searches are performed with the NBLAST nucleotide program parameters set, e.g., for score=100, wordlength=12 to obtain nucleotide sequences homologous to a nucleic acid molecules of the present invention. BLAST protein searches are performed with the XBLAST program parameters set, e.g., to score 50, wordlength=3 to obtain amino acid sequences homologous to a protein molecule of the present invention. To obtain gapped alignments for comparison purposes, Gapped BLAST are utilized as described in Altschul et al., 1997, Nucleic Acids Res. 25:3389 3402. Alternatively, PSI BLAST is used to perform an iterated search which detects distant relationships between molecules (Id.). When utilizing BLAST, Gapped BLAST, and PSI Blast programs, the default parameters of the respective programs (e.g., of XBLAST and NBLAST) are used (see, e.g., the NCBI website). Another preferred, non limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used.

The percent identity between two sequences is determined using techniques similar to those described above, with or without allowing gaps. In calculating percent identity, typically only exact matches are counted.

Argininosuccinate synthetase included in methods and compositions of the present invention is optionally produced using recombinant nucleic acid technology. Argininosuccinate synthetase production includes introducing a recombinant expression vector encompassing a DNA sequence encoding argininosuccinate synthetase.

A nucleic acid sequence encoding argininosuccinate synthetase introduced into a host cell to produce argininosuccinate synthetase encodes SEQ ID NO: 1. In embodiments of the present invention, the nucleic acid sequence identified herein as SEQ ID NO: 2 encodes SEQ ID NO: 1 and is included in an expression vector and expressed to produce argininosuccinate synthetase.

It is appreciated that due to the degenerate nature of the genetic code, nucleic acid sequences substantially identical to SEQ ID NO: 2 encode argininosuccinate synthetase and variants of argininosuccinate synthetase, and that such alternate nucleic acids may be included in an expression vector and expressed to produce argininosuccinate synthetase and variants of argininosuccinate synthetase.

A nucleic acid sequence which is substantially identical to SEQ ID No. 2 is characterized as having a complementary nucleic acid sequence capable of hybridizing to SEQ ID No. 2 under high stringency hybridization conditions.

The term "nucleic acid" refers to RNA or DNA molecules having more than one nucleotide in any form including single-stranded, double-stranded, oligonucleotide or polynucleotide. The term "nucleotide sequence" refers to the ordering of nucleotides in an oligonucleotide or polynucleotide in a single-stranded form of nucleic acid.

The term "complementary" refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA- is 100% complementary to a region of the nucleotide sequence 5'-TTAGCTGG-3'.

The terms "hybridization" and "hybridizes" refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. The term "stringency of hybridization conditions" refers to conditions of temperature, ionic strength, and composition of a hybridization medium with respect to particular common additives such as formamide and Denhardt's solution. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002. High stringency hybridization conditions are those which only allow hybridization of substantially complementary nucleic acids. Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize.

The terms "specific hybridization" and "specifically hybridizes" refer to hybridization of a particular nucleic acid to a target nucleic acid without substantial hybridization to nucleic acids other than the target nucleic acid in a sample.

Stringency of hybridization and washing conditions depends on several factors, including the Tm of the probe and target and ionic strength of the hybridization and wash conditions, as is well-known to the skilled artisan. Hybridization and conditions to achieve a desired hybridization stringency are described, for example, in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002.

An example of high stringency hybridization conditions is hybridization of nucleic acids over about 100 nucleotides in length in a solution containing 6×SSC, 5× Denhardt's solution, 30% formamide, and 100 micrograms/ml denatured salmon sperm at 37° C. overnight followed by washing in a solution of 0.1×SSC and 0.1% SDS at 60° C. for 15 minutes. SSC is 0.15M NaCl/0.015M Na citrate. Denhardt's solution is 0.02% bovine serum albumin/0.02% FICOLL/0.02% polyvinylpyrrolidone. Under highly stringent conditions, SEQ ID No. 2 will hybridize to the complement of substantially identical targets and not to unrelated sequences.

The term "expression vector" refers to a recombinant vehicle for introducing a nucleic acid encoding argininosuccinate synthetase into a host cell where the nucleic acid is expressed to produce argininosuccinate synthetase. In particular embodiments, an expression vector including SEQ ID NO: 2 or a substantially identical nucleic acid sequence is expressed to produce argininosuccinate synthetase in cells containing the expression vector.

In addition to one or more nucleic acids encoding argininosuccinate synthetase, one or more nucleic acid sequences encoding additional proteins can be included in an expression vector. For example, such additional proteins include non-argininosuccinate synthetase proteins such as reporters, including, but not limited to, beta-galactosidase, green fluorescent protein and antibiotic resistance reporters.

Expression vectors are known in the art and include plasmids and viruses, for example An expression vector contains a nucleic acid that includes segment encoding a polypeptide of interest operably linked to one or more regulatory elements that provide for transcription of the segment encoding the polypeptide of interest. Such regulatory elements include, but are not limited to, promoters, terminators, enhancers, origins of replication and polyadenylation signals.

In particular embodiments, the recombinant expression vector encodes at least argininosuccinate synthetase of SEQ ID NO: 1, a protein having at least 95% identity to SEQ ID NO: 1, or a protein encoded by a nucleic acid sequence substantially identical to SEQ ID NO: 2.

Expression of argininosuccinate synthetase using a recombinant expression vector is accomplished by introduction of the expression vector into a eukaryotic or prokaryotic host cell expression system such as an insect cell, mammalian cell, yeast cell, bacterial cell or any other single or multicellular organism recognized in the art. Host cells are optionally primary cells or immortalized derivative cells Immortalized cells are those which can be maintained in-vitro for at least 5 replication passages.

Host cells containing the recombinant expression vector are maintained under conditions wherein argininosuccinate synthetase is produced. Host cells may be cultured and maintained using known cell culture techniques such as described in Celis, Julio, ed., 1994, Cell Biology Laboratory Handbook, Academic Press, N.Y. Various culturing conditions for these cells, including media formulations with regard to specific nutrients, oxygen, tension, carbon dioxide and reduced serum levels, can be selected and optimized by one of skill in the art.

Argininosuccinate synthetase optionally has an amino acid sequence identical to an argininosuccinate synthetase found in nature. Illustratively, argininosuccinate synthetase has the sequence of SEQ ID NO: 1. Some embodiments of the invention use an argininosuccinate synthetase variant optionally with an amino acid sequence that differs from a sequence found in nature. Variants of argininosuccinate synthetase are optionally created by site directed mutagenesis of a wild type nucleic acid sequence encoding argininosuccinate synthetase. Illustratively, the sequence of SEQ ID NO: 2 is used as a source nucleic acid sequence for site-directed mutagenesis.

In some embodiments, an argininosuccinate synthetase variant is created that maintains the LPS binding site, but is altered elsewhere in the molecule. A variant is optionally a truncated form of argininosuccinate synthetase. A truncated argininosuccinate synthetase optionally retains the wild-type LPS binding site, but is truncated elsewhere in the molecule. Optionally, a variant also, or independently, alters the LPS binding site so as to increase or decrease the argininosuccinate synthetase affinity for LPS. Methods of site-directed mutagenesis and screening for affinity between molecules are well known in the art.

Argininosuccinate synthetase is optionally PEGylated. A protein is PEGylated when bound either covalently or otherwise to one or more molecules of polyethylene glycol (PEG) either directly or through a linker. Covalent attachment of the inert, non-toxic, biodegradable polymer PEG, to molecules has important applications in biotechnology and medicine. PEGylation of biologically and pharmaceutically active proteins typically improve pharmacokinetics, resulting in sustained duration, improve safety (e.g. lower toxicity, immunogenicity and antigenicity), increase efficacy, decrease dosing frequency, improve drug solubility and stability, reduce proteolysis, and facilitate controlled drug release (Roberts et al., 2002, *Adv Drug Deliv Rev,* 54:459-76; Harris & Chess, 2003, *Nat Rev Drug Discov,* 2:214-221). Each of these positive attributes of PEGylation of proteins is attributable to the alteration in pharmacokinetics of the protein. In fact, it is recognized in the art that PEGylation reduces biological activity in vitro. This reduction in activity is overcome in vivo by longer therapeutic lifetime. (See Jevsevar S, et al., *Biotechnol. J.,* 2010; 5:113-128.)

The inventors unexpectedly discovered that PEGylation of argininosuccinate synthetase not only increases stability of the protein, but also improves the enzymatic activity of argininosuccinate synthetase. As such, some embodiments of the invention include administration of a PEGylated argininosuccinate synthetase which is shows unexpectedly superior efficacy in vivo and in vitro.

Argininosuccinate synthetase is optionally homogenously or heterogeneously PEGylated with PEG molecules ranging from 3 to 1000 PEG units, optionally from 3 to 100 PEG units, optionally from 3 to 50 PEG units, or any value or subrange therebetween. The total molecular weight of PEG molecules bound to argininosuccinate synthetase is optionally from 300 Daltons to 50,000 Daltons or any range or subdivision therebetween.

PEG molecules used to PEGylate argininosuccinate synthetase are optionally linear, branched, or a combination thereof. In some embodiments, only linear PEG molecules are used to PEGylate argininosuccinate synthetase. In some embodiments, only branched PEG molecules are used to PEGylate argininosuccinate synthetase. The relative ratios of unbranched to branched PEG molecules are appreciated to be any range suitable for improving the stability of the resulting PEGylated argininosuccinate synthetase. Illustratively, the ratio of unbranched to branched PEG ranges from 0.001:1 to 1:0.001, or any value or range therebetween.

The extend of PEGylation on each individual argininosuccinate synthetase molecule optionally varies. The ratio of argininosuccinate synthetase to PEG is optionally anywhere from 1:1 to 1:500, or any value or range therebetween. In some embodiments, the ratio of argininosuccinate synthetase to PEG is from 1:1 to 1:100, optionally 1:1 to 1:10, optionally, 1:1 to 1:5. In some embodiments the ratio of argininosuccinate synthetase to PEG is 1:10. These ranges illustrate molar ratios whereby one mole of argininosuccinate synthetase is bound to anywhere from 1 to 500 moles of PEG species.

Numerous PEG species are operable to PEGylate argininosuccinate synthetase. Illustrative examples include PEG-chlorotriazine, PEG succinimidyl succinate (SS-PEG), succinimidyl carbonate PEG (SC-PEG), the N-Hydroxysuccinimide PEGs including methyl succinimidyl PEG (MS-PEG) and trimethyl succinimidyl PEG (TMS-PEG), as well as other PEG molecules known in the art. Specific examples of PEG molecules operable herein include $MS\text{-}PEG_{12}$ and $TMS\text{-}PEG_{12}$.

PEGylation of argininosuccinate synthetase is illustratively random or site-specific. Random PEGylation is illustratively achieved by a linker that interacts with proteins to form an amide linkage or a urethane linkage. Amide linkages allow stable PEG binding to lysine residues as well as the protein N-terminus. Urethane linkages are capable of interacting with lysine and histidine residues. A urethane linkage may be relatively unstable compared to an amide linkage, but may have the advantage in the preparation of pro-drug or controlled-release formulations of PEGylated argininosuccinate synthetase.

PEGylation of argininosuccinate synthetase is optionally site-specific meaning that the preparation of PEGylated argininosuccinate synthetase typically has increased uniformity over random PEGylation. PEGylation is optionally specific to the N-terminus or other location on argininosuccinate synthetase or a variant thereof. Techniques for N-terminal and cysteine-specific PEGylation are well known in the art. N-terminal PEGylation is illustratively achieved with a PEG-aldehyde reagent. PEGylation of thiol groups are illustratively achieved using thiol specific reagents such as maleimide, pyridyl disulfide, and vinyl sulfone, among others known in the art. Illustrative examples of techniques suitable for site-directed PEGylation include transient denaturing conditions of Veronese, F M, et al., *Bioconjug. Chem.*, 2007; 18:1824-1830. Alternatively, the methods presented in U.S. Patent Application Publication Nos: 2010/0247508 or 2009/047500 may be used. In some embodiments, free cysteines (or other specific amino acid, or amino acid chemistries) are incorporated into the sequence of argininosuccinate synthetase such as by site directed mutagenesis so as to create PEGylation sites. Another optional method for site-directed PEGylation is that of enzymatic PEGylation. Enzymatic PEGylation of PEG-alkylamine reagents is illustratively described by Sato, H, *Adv. Drug Deliv. Rev.*, 2002; 54:487-504.

The extent of PEGylation on argininosuccinate synthetase is optionally homogenous or heterogeneous throughout a therapeutically effective solution of PEGylated argininosuccinate synthetase. In some embodiments, more or either the linear or branched PEG is present in a sample. As such a solution of argininosuccinate synthetase optionally includes argininosuccinate synthetase molecules with uniform or varying PEGylation type, extent, or mass.

Methods of preventing or treating a disease or disorder characterized by signs and/or symptoms of exposure to bacterial endotoxin are provided according to the present invention which includes administering a therapeutically effective amount of a composition including argininosuccinate synthetase to a subject in need thereof. In particular embodiments, a composition according to the present invention is administered to a subject having a disease or disorder or at risk for a disease or disorder characterized by exposure of the subject to bacterial endotoxin.

Broadly described, a method according to embodiments of the present invention includes administration of argininosuccinate synthetase to an organism, a cell or tissue, in vitro or in vivo.

Administration of argininosuccinate synthetase is optionally followed by assay of the effects of argininosuccinate synthetase in the subject organism, cell or tissue.

The term "therapeutically effective amount" as used herein is intended to mean an amount of an inventive composition which is effective to alleviate, ameliorate or prevent a symptom or sign of a condition to be treated. In particular embodiments, a therapeutically effective amount is an amount which has a beneficial effect in a subject having signs and/or symptoms of exposure to bacterial endotoxin.

Thus, for example, in particular embodiments, treatment of a subject to prevent or treat effects of exposure to bacterial endotoxin in the subject is characterized by prevention or amelioration of pathogenic effects of bacterial endotoxin. Amelioration of signs and symptoms of sepsis and/or endotoxic shock is assessed by techniques known in the art and described herein.

Signs and symptoms of exposure to bacterial endotoxin include, but are not limited to, fever, rapid heartbeat, rapid respiration, low blood pressure, local or generalized Shwartzman reaction and organ failure.

The term "subject" refers to any individual to whom a composition of the present invention is administered. The term "subject" includes mammals and birds, particularly humans, non-human primates, cats, dogs, cows, horses, rodents, pigs, sheep, goats and poultry. A subject in need is a subject suffering from a form of bacterial sepsis. A subject in need optionally suffers or suffered: an intravenous puncture; perforated, compromised, or ruptured intra-abdominal or pelvic structure; bacteruria; or other infection illustratively with the at least one of the pathogenic bacteria *Streptococcus pneumonia, Neisseria meningitides, Staphylococcus aureus, Hemophilus influenzae, Klebsiella pneumonia, Legionella* spp., *Streptococcus agalactiae, E. coli, Klebsiella pneumoniae, Listeria monocytogenes, Enterococcus* spp., *Streptococcus pyogenes, Erysipelothrix rhusiopathiae, Aeromonas hydrophila, Vibrio vulnificus, Clostridium perfringens, Salmonella* spp., or other pathogenic Gram-negative bacteria known in the art. When infection is by a bacteria normally found in a subject, a subject in need is a subject suffering a bacterial infection in a compartment other than that in which the bacteria is normally found. As such, the term "infected with" means the presence of a Gram-negative bacteria in a biological compartment where the bacteria is not normally found.

The amount of a composition of the present invention administered to a subject and the route of administration depends on factors such as the severity of an infection affecting the subject, the activity and rate of excretion of the argininosuccinate synthetase, and the general physical characteristics of the subject including age, gender and body weight. One of skill in the art could determine a therapeutically effective amount and route of administration in view of these and other considerations typical in medical practice.

Amounts of argininosuccinate synthetase used in a method to inhibit bacterial endotoxin will be determined by one of skill in the art without undue experimentation.

In general, a therapeutically effective amount of argininosuccinate synthetase in a composition is in the range of about 0.001mg/kg-100 mg/kg body weight. In particular embodiments, a therapeutically effective amount of argininosuccinate synthetase in a composition is in the range of about 0.01-10 mg/kg, and in further embodiments, a therapeutically effective amount of argininosuccinate synthetase in a composition is in the range of about 0.1-5 mg/kg. A therapeutically effective amount of a composition of the present invention may be manufactured and/or administered in single or multiple unit dose forms.

In some embodiments, a method according to the present invention includes administering a therapeutic agent in addition to argininosuccinate synthetase to a subject. A therapeutic agent may be any of various agents suitable for use in conjunction with amelioration of infection by endotoxin-containing bacteria or exposure to bacterial endotoxin. For example, a therapeutic agent is an antibiotic in one embodiment of the present invention. Antibiotics include, for example, aminoglycosides, amoxicillin, amphenicols, ansamycins, antibiotic polypeptides, beta-lactams, carbapenems, cephalosporins, cephamycins, oxacephems, lincosamides, macrolides, monobactams, nitrofurans, quinolones, sulfonamides, sulfones and tetracyclines.

In particular embodiments, a composition is provided according to the present invention which includes argininosuccinate synthetase and a pharmaceutically acceptable carrier.

The term "pharmaceutically acceptable carrier" as used herein refers to a carrier or diluent that is generally non-toxic to an intended recipient and which does not significantly inhibit activity of argininosuccinate synthetase or other active agent included in the composition.

A composition according to the present invention generally includes about 0.1-99% of argininosuccinate synthetase.

Argininosuccinate synthetase is included in a composition of the present invention in the form of a free acid or free base in particular embodiments. In further embodiments, argininosuccinate synthetase is included in a composition in the form of a pharmaceutically acceptable salt such as an acid or base addition salt. A pharmaceutically acceptable salt refers to any salt form of argininosuccinate synthetase that is generally non-toxic to an intended recipient and which does not significantly inhibit activity of the argininosuccinate synthetase or other active agent included in the composition. Argininosuccinate synthetase is included in a composition in the form of a hydrate in embodiments of the present invention.

An argininosuccinate synthetase prodrug is included in a composition according to particular embodiments of the present invention. An argininosuccinate synthetase prodrug is a form of argininosuccinate synthetase covalently bound to a moiety which is released from argininosuccinate synthetase yielding the intact active argininosuccinate synthetase. Prodrug forms are well known in the art as exemplified in Sloan, K. B., Prodrugs, M. Dekker, New York, 1992; and Testa, B. and Mayer, J. M., Hydrolysis in drug and prodrug metabolism: chemistry, biochemistry, and enzymology, Wiley-VCH, Zurich, 2003.

More than one form of argininosuccinate synthetase is included in a composition according to embodiments of the present invention. Thus, for example, in particular embodiments human argininosuccinate synthetase and one or more variants of human argininosuccinate synthetase are both included in a composition.

Argininosuccinate synthetase is administered to a subject as an isolated argininosuccinate synthetase protein according to embodiments of the present invention. The term "isolated argininosuccinate synthetase protein" indicates that the argininosuccinate synthetase protein has been separated from biological materials, such as cells, cellular debris and other proteins, which may be present in the system in which the argininosuccinate synthetase protein was produced. The term "isolated" argininosuccinate synthetase protein may, but does not necessarily, indicate that the argininosuccinate synthetase protein is purified. Purified argininosuccinate synthetase protein included in methods and compositions of the present invention contains least about 1-100% of the mass, by weight, such as about 25%, 50%, 75%, 85%, 95%, 99% or greater than about 99% of the mass, by weight, of the protein included.

In some embodiments, an expression vector including a nucleic acid encoding argininosuccinate synthetase is administered to a subject to produce the argininosuccinate synthetase protein in vivo.

A composition according to the present invention may be formulated in various forms. A composition formulated for oral administration may be a solid, semi-solid or liquid formulation prepared according to methods known in the art and including any of various conventional pharmaceutical ingredients.

Numerous delivery systems are known and can be used to deliver argininosuccinate synthetase to a subject, illustratively including liposomes and nanoparticles such as nanospheres, nanodendrimers, nanocolloids, nanodots, nanocolumns, and combinations of these. Further description of liposomes and methods relating to their preparation and use may be found in Liposomes: A Practical Approach (The Practical Approach Series, 264), V. P. Torchilin and V. Weissig (Eds.), Oxford University Press; 2nd ed., 2003. Further aspects of nanoparticles are described in S. M. Moghimi et al., FASEB J. 2005, 19, 311-30.

Solid dosage forms for oral administration include capsules, tablets, pills, powders, and granules. In such solid dosage forms, argininosuccinate synthetase is admixed with at least one pharmaceutically acceptable carrier such as a filler or extender, as for example, starches, lactose, sucrose, glucose, mannitol, and silicic acid; a binder, as for example, carboxymethylcellulose, alignates, gelatin, polyvinylpyrrolidone, sucrose, and acacia; a humectant, as for example, glycerol; a disintegrating agent, as for example, agar-agar, calcium carbonate, plant starches such as potato or tapioca starch, alginic acid, certain complex silicates, and sodium carbonate; a solution retarder, as for example, paraffin; an absorption accelerator, as for example, quaternary ammonium compounds; a wetting agent, as for example, cetyl alcohol, glycerol monostearate, and glycols; an adsorbent, as for example, kaolin and bentonite; a buffering agent, such as sodium citrate and dicalcium phosphate; and a lubricant, as for example, talc, calcium stearate, magnesium stearate, solid polyethylene glycols and sodium lauryl sulfate. Mixtures of these or other pharmaceutically acceptable carriers may also be included in embodiments of a composition of the present invention.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner Examples of embedding compositions which can be used are polymeric substances and waxes. The active compounds can also be in micro-encapsulated form, if appropriate, with one or more of the above-mentioned excipients.

The enteric coating is typically a polymeric material. Preferred enteric coating materials have the characteristics of being bioerodible, gradually hydrolyzable and/or gradually water-soluble polymers. The amount of coating material applied to a solid dosage generally dictates the time interval between ingestion and drug release. A coating is applied with to a thickness such that the entire coating does not dissolve in the gastrointestinal fluids at pH below 3 associated with stomach acids, yet dissolves above pH 3 in the small intestine environment. It is expected that any anionic polymer exhibiting a pH-dependent solubility profile is readily used as an enteric coating in the practice of the present invention to achieve delivery of the active to the lower gastrointestinal tract. The selection of the specific enteric coating material depends on properties such as resistance to disintegration in the stomach; impermeability to gastric fluids and active agent diffusion while in the stomach; ability to dissipate at the target intestine site; physical and chemical stability during storage; non-toxicity; and ease of application.

Suitable enteric coating materials illustratively include cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonium methylacrylate, ethyl acrylate, methyl methacrylate and/or ethyl; vinyl polymers and copolymers such as polyvinyl pyrrolidone, polyvinyl acetate, polyvinylacetate phthalate, vinylacetate crotonic acid copolymer, and ethylene-vinyl acetate copolymers; shellac; and combinations thereof. A particular enteric coating material is those acrylic acid polymers and copolymers available under the trade name EUDRAGIT, Roehm Pharma (Germany) The EUDRAGIT series L, L-30D S copolymers, and cross-linked polymers, see for example U.S. Pat. No. 6,136,345, are suitable in particular applications since these are insoluble in the stomach and dissolve in the intestine.

The enteric coating optionally contains a plasticizer to prevent the formation of pores and cracks that allow the penetration of the gastric fluids into the solid dosage. Suitable plasticizers illustratively include, triethyl citrate (Citroflex 2), triacetin (glyceryl triacetate), acetyl triethyl citrate (Citroflex A2), Carbowax 400 (polyethylene glycol 400), diethyl phthalate, tributyl citrate, acetylated monoglycerides, glycerol, fatty acid esters, propylene glycol, and dibutyl phthalate. In particular, a coating composed of an anionic carboxylic acrylic polymer typically contains approximately 10% to 25% by weight of a plasticizer, particularly dibutyl phthalate, polyethylene glycol, triethyl citrate and triacetin. The coating can also contain other coating excipients such as detackifiers, antifoaming agents, lubricants (e.g., magnesium stearate), and stabilizers (e.g., hydroxypropylcellulose, acids and bases) to solubilize or disperse the coating material, and to improve coating performance and the coated product.

The enteric coating is applied to a solid dosage using conventional coating methods and equipment. For example, an enteric coating can be applied to a solid dosage using a coating pan, an airless spray technique, fluidized bed coating equipment, or the like. Detailed information concerning materials, equipment and processes for preparing coated dosage forms may be found in Pharmaceutical Dosage Forms: Tablets, eds. Lieberman et al. (New York: Marcel Dekker, Inc., 1989), and in L. V. Allen, Jr. et al., Ansel's Pharmaceutical Dosage Forms and Drug Delivery Systems, 8th Ed. (Philadelphia, Pa.: Lippincott, Williams & Wilkins, 2004).

Liquid dosage forms for oral administration include a pharmaceutically acceptable carrier formulated as an emulsion, solution, suspension, syrup, or elixir in particular embodiments. In addition to argininosuccinate synthetase, the liquid dosage forms may contain one or more pharmaceutically acceptable carriers commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and/or other such conventional pharmaceutical ingredients.

A composition formulated for oral administration can also include adjuvants, such as wetting agents, emulsifying and suspending agents, sweetening, flavoring, and perfuming agents.

Suspensions, in addition to argininosuccinate synthetase, may contain suspending agents, as for example, ethoxylated isostearyl alcohols, polyoxyethylene sorbitol and sorbitol esters, microcrystalline cellulose, aluminum metahydroxide, bentonite, agar-agar or tragacanth, or mixtures of these substances, and/or other such conventional pharmaceutical ingredients.

In particular embodiments, a composition including argininosuccinate synthetase of the present invention is formulated as a physiologically acceptable sterile aqueous or nonaqueous solution, dispersion, suspension, emulsion, or sterile powder for reconstitution into a sterile injectable solution or dispersion. Examples of suitable aqueous and nonaqueous carriers, include diluents, solvents, and vehicles such as water, ethanol, polyols such as propylene glycol, polyethylene glycol, glycerol, and the like, and suitable mixtures thereof; vegetable oils such as olive oil; and injectable organic esters such as ethyloleate. Proper fluidity can be maintained, for example, by the use of a coating such as lecithin, by the maintenance of the required particle size in the case of dispersions, and by the use of surfactants, such as sodium lauryl sulfate.

Such formulations are administered by a suitable route including parenteral and oral administration. Administration may include systemic or local injection, such as intravenous injection.

A composition of the present invention may also contain one or more adjuvants such as preserving, wetting, emulsifying, and dispensing agents. Prevention of the action of microorganisms can be ensured by various antibacterial and antifungal agents, for example, parabens, chlorobutanol, phenol and sorbic acid. It may also be desirable to include an isotonic agent, exemplified by sugars and sodium chloride. Prolonged delivery of an injectable pharmaceutical form can be achieved by the use of agents delaying absorption, for example, aluminum monostearate and gelatin.

Detailed information concerning materials, equipment and processes for preparing and manufacturing various dosage forms may be found in Pharmaceutical Dosage Forms: Tablets, eds. H. A. Lieberman et al., New York: Marcel Dekker, Inc., 1989, and in L. V. Allen, Jr. et al., Ansel's Pharmaceutical Dosage Forms and Drug Delivery Systems, 8th Ed., Philadelphia, Pa.: Lippincott, Williams & Wilkins, 2004. Further examples and details of pharmacological formulations and ingredients are found in standard references such as: A. R. Gennaro, Remington: The Science and Practice of Pharmacy, Lippincott Williams & Wilkins, 20th ed., 2003; L. V. Allen, Jr. et al., Ansel's Pharmaceutical Dosage Forms and Drug Delivery Systems, 8th Ed., Philadelphia, Pa., Lippincott, Williams & Wilkins, 2004; and J. G. Hardman et al., Goodman & Gilman's The Pharmacological Basis of Therapeutics, McGraw-Hill Professional, 10th ed., 2001.

A composition including argininosuccinate synthetase may be administered by a systemic route and/or by a local route. Suitable routes of administration illustratively include intravenous, oral, buccal, parenteral, intrathecal, intracerebroventricular, intraperitoneal, ocular, intraocular, rectal, vaginal, subcutaneous, intradermal, intramuscular, topical, intranasal, otic and mucosal.

In further embodiments of inventive methods, argininosuccinate synthetase presence, levels, and/or activity are assessed in a sample suspected of exposure to bacterial endotoxin. It is a finding of the present invention that argininosuccinate synthetase levels and activity are elevated over normal levels and activities in samples obtained from subjects exposed to bacterial endotoxin.

Assays for argininosuccinate synthetase levels and/or activity are optionally performed on any material suspected of having been exposed to bacterial endotoxin, such as a sample from a subject, cultured primary cells and/or tissues or cell lines. Assays for argininosuccinate synthetase levels and/or activity are optionally performed using any of various assay methods illustratively include enzyme-linked immunosorbent assay (ELISA), flow cytometry, immunoblot, immunoprecipitation, immunocytochemistry, radioimmunoassay, RT-PCR, northern blot hybridization, dot blot hybridization, RNAase protection, or a combination of any of these. Assay methods may be used to obtain qualitative and/or quantitative results. Specific details of suitable assay methods for both qualitative and quantitative assay of a sample are described in standard references, illustratively including E. Harlow and D. Lane, Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; B. K. C. Lo, Antibody Engineering: Methods and Protocols, Methods in Molecular Biology, Humana Press, 2003; F. M. Ausubel et al., Eds., Short Protocols in Molecular Biology, Current Protocols, Wiley, 2002; S. Klussman, Ed., The Aptamer Handbook: Functional Oligonucleotides and Their Applications, Wiley, 2006; Ormerod, M. G., Flow Cytometry: a practical approach, Oxford University Press, 2000; Givan, A. L., Flow Cytometry: first principles, Wiley, New York, 2001; Gorczyca, W., Flow Cytometry in Neoplastic Hematology: morphologic-immunophenotypic correlation, Taylor & Francis, 2006; and J. Sambrook and D. W. Russell, Molecular Cloning: A Laboratory Manual, Cold Spring Harbor Laboratory Press, 3rd Ed., 2001, or by methods described herein.

A sample from a subject are illustratively a sample of a tissue, cells, a bodily fluid that may or may not include cells, or a sample obtained from the environment such as soil, water, or other environmental sample. Illustrative examples of a sample include blood, plasma, serum, saliva, mucous, semen, tears, lymph, and urine. As such, obtaining a sample is by any method known in the art to acquire a sample illustratively including venipuncture to obtain whole blood whereby serum is illustratively achieved by clotting the blood and removing the soluble fraction, plasma is obtained by centrifugation of whole blood and removing the upper plasma section, or other standard collection techniques.

A method of treating exposure to bacterial endotoxin is applicable to a human subject as well as a non-human subject. In particular embodiments, a method of treating exposure to bacterial endotoxin includes administration of argininosuccinate synthetase to a human, or non-human subject such as non-human primates, cats, dogs, cows, horses, rodents, pigs, sheep, goats and poultry or other non-human mammal or bird.

Embodiments of inventive compositions and methods are illustrated in the following examples. These examples are provided for illustrative purposes and are not considered limitations on the scope of inventive compositions and methods.

EXAMPLES

Reagents

Lipopolysaccharide (LPS) from *Escherichia coli* O111:B4 and *Salmonella enterica typhimurium* are purchased from Sigma (St. Louis, Mo., USA). The rat TNF-α and CRP ELISA kits are purchased from eBioscience (San Diego, Calif.), and BioVendor (Modrice, Czech Rep.) respectively. Antibodies against polyhistidine, αII-spectrin and LPS core (clone WN1 222-5) are purchased from Santa Cruz Biotechnology (Santa Cruz, Calif.), Biomol Co. (Plymouth Meeting, Pa.), and HyCult Biotechnology (Uden, Netherlands) respectively. Antibodies against human ASS are produced at Banyan Biomarkers, Inc. by standard techniques.

Example 1

LPS Treatment Induces Serum Accumulation of Endogenous ASS Biomarker in vivo

Adult male Sprague-Dawley rats (200-225 g) and Balb/c mice (19-22 g) (Harlan Laboratories Inc., Indianapolis, Ind.) are housed under constant temperature (22° C.) and humidity with 12 hours light/dark cycle with access to chow and water ad libitum.

Levels of endogenous ASS in serum are determined after LPS treatment in combination with liver injury priming agent D-galactosamine (D-Gal). Lipopolysaccharide from *E. coli* (LPS, 10 µg/kg) plus D-galactosamine (D-Gal, 500 mg/kg), LPS alone (100 µg/kg), or saline are injected intraperitoneally (i.p.) in Sprague-Dawley rats. Blood is collected from heart of anesthetized animals 1 h, 2 h, 3 h, 24 h and 72 h after the treatment, using at least 3 rats for each time point. As seen in FIG. 1, ASS is extremely sensitive marker of endotoxin-induced liver injury and significantly increased in serum within 1 hour following injection of endotoxin and D-galactosamine (FIG. 1A). The ASS accumulation in blood attains 1000 ng/ml in rats surviving 24 hours after treatment. In rats recovering from injection, ASS serum levels decline at 72 hours to nearly baseline, but are still elevated over control, saline-treated rats (FIG. 1A). When LPS is injected at 10× fold higher dose without D-Gal, serum ASS increases exhibited a similar profile but the levels are of significantly lower magnitude than in the presence of D-galactosamine (FIG. 1B).

Example 2

Recombinant Argininosuccinate Synthetase Cloning, Protein Expression and Purification The coding region (residues 1-412) of the human argininosuccinate synthetase gene (GenBank accession No. BC009243.2; Swiss-Prot name ASSY_HUMAN) is amplified using original clone from Open Biosystems (Huntsville, Ala.) (Clone ID: 3010137) as a template for PCR amplification. Primers are as follows: forward 32-mer (including ATG), 5'-ATGTCCAGCAAAGGCTCCGTGGTTCTGGC-CTA -3'; reverse 50-mer (created to contain a HindIII site and a C-terminal His-tag fusion), 5'-TATAAAGCTTTCAATGGTGATGGTGATGAT-GTTTGGCAGTGACCTTGCTC-3'. Thirty cycles of PCR are performed as the following: denaturation for 1 min at 94° C., annealing for 1 min at 53° C., and elongation for 2 min at 72° C. This results in the amplification of a single product of the predicted size for human ASS1-6× His fusion (1254 base pairs) that is gel-purified and directly ligated into pETBlue-1 vector using AccepTor Vector kit (Novagen, Madison, Wis.). The correct sequence of the cDNA is verified by Sanger sequencing. The coding region (residues 1-412) of the human argininosuccinate synthetase gene (GenBank accession No. BC009243.2; Swiss-Prot name ASSY_HUMAN) is amplified using original clone from Open Biosystems (Huntsville, Ala.) (Clone ID: 3010137) as a template for PCR amplification. Primers are as follows: forward 32-mer (including ATG), 5'-ATGTCCAG-CAAAGGCTCCGTGGTTCTGGCCTA -3'(SEQ ID NO. 3); reverse 50-mer (created to contain a HindIII site and a C-terminal His-tag fusion), 5'-TATAAAGCTTTCAATGGT- GATGGTGATGATGTTTGGCAGTGACCTTGCTC-3' (SEQ ID NO. 4). Thirty cycles of PCR are performed as the following: denaturation for 1 min at 94° C., annealing for 1 min at 53° C., and elongation for 2 min at 72° C. This results in the amplification of a single product of the predicted size for human ASS1-6× His fusion (1254 base pairs) that is gel-purified and directly ligated into pETBlue-1 vector using AccepTor Vector kit (Novagen, Madison, Wis.). The correct sequence of the cDNA is verified by Sanger sequencing.

For the inducible expression of ASS1 cDNA under the control of the T7lac promoter, the construct is transformed into the Tuner(DE3)pLacI E. coli strain (Novagen). After transformation by a standard heat shock technique and liquid-culture growth in Luria Broth (LB) using standard methods, expression of recombinant human argininosuccinate synthetase (rASS) is induced by the addition of isopropyl-thiogalactopyranoside (IPTG). Induction conditions (16 hr at 18° C. in the presence of 0.5 mM IPTG) are optimized to achieve the highest yield of soluble rASS. After harvesting, the cell pellets are subjected to freezing at −70° C. and thawing at 37° C. and suspended in SoluLyse lysis buffer (GenLantis, San Diego, Calif.) supplemented with protease inhibitor and DNAase. rASS is purified using affinity chromatography on HisPur Cobalt spin column (Pierce, Rockford, Ill.). The binding/wash buffer contains 50 mM sodium phosphate, 300 mM NaCl, and 10 mM imidazole pH 7.4. The elution buffer is identical except that the imidazole concentration is raised to 150 mM. The protein is concentrated and the buffer exchanged for phosphate-buffered saline (PBS) using U-Tube concentrators (Novagen). The final buffer solution at pH 7.4 is supplemented with 1 mM citrulline and 1 mM aspartate to preserve protein solubility and catalytic activity.

Figure 2:
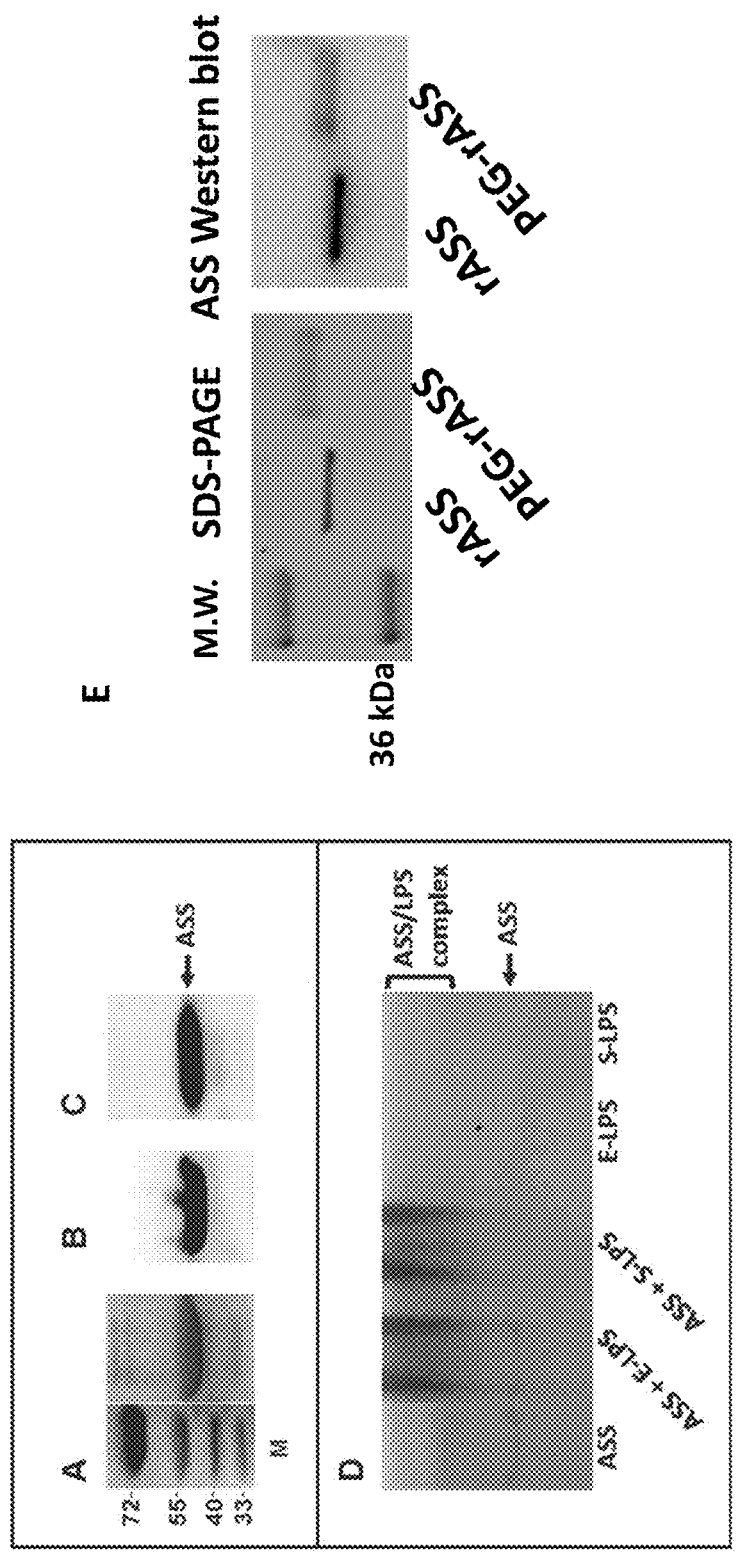
FIG. 2 are examples of rASS or PEGylated-rASS illustrated following SDS-PAGE stained with either Coomassie blue or visualized by western blotting.

Affinity purified protein is ~95% pure protein as indicated by Coomassie Blue staining (FIG. 2A).

PEGylated-rASS is prepared using either MS-PEG$_{12}$-or TMS-PEG$_{12}$ from Pierce Biotechnology, Rockford, Ill. Briefly, a solution of MS-PEG12-or TMS-PEG12 is prepared in anhydrous dimethylformamide and added dropwise to a solution of rASS protein at ratios of 200:1 or 400:1, PEG to ASS respectively. The reaction mixture is incubated at room temperature for 0.5 h and the solution of protein is purified on a calibrated Desalt Spin Column by centrifugation at 1,000×g for 5 min. Purity and completion of reaction is evaluated using SDS-PAGE. (FIG. 2A, E) Immunogenic purity of rASS is established by western blot with antibody against 6× His (FIG. 2B, E) as well as polyclonal antibody (ASS1) raised in rabbits against an ASS-derived peptide (FIG. 2C, E).

Example 3

Bacterial Growth Kinetics

Figure 3:
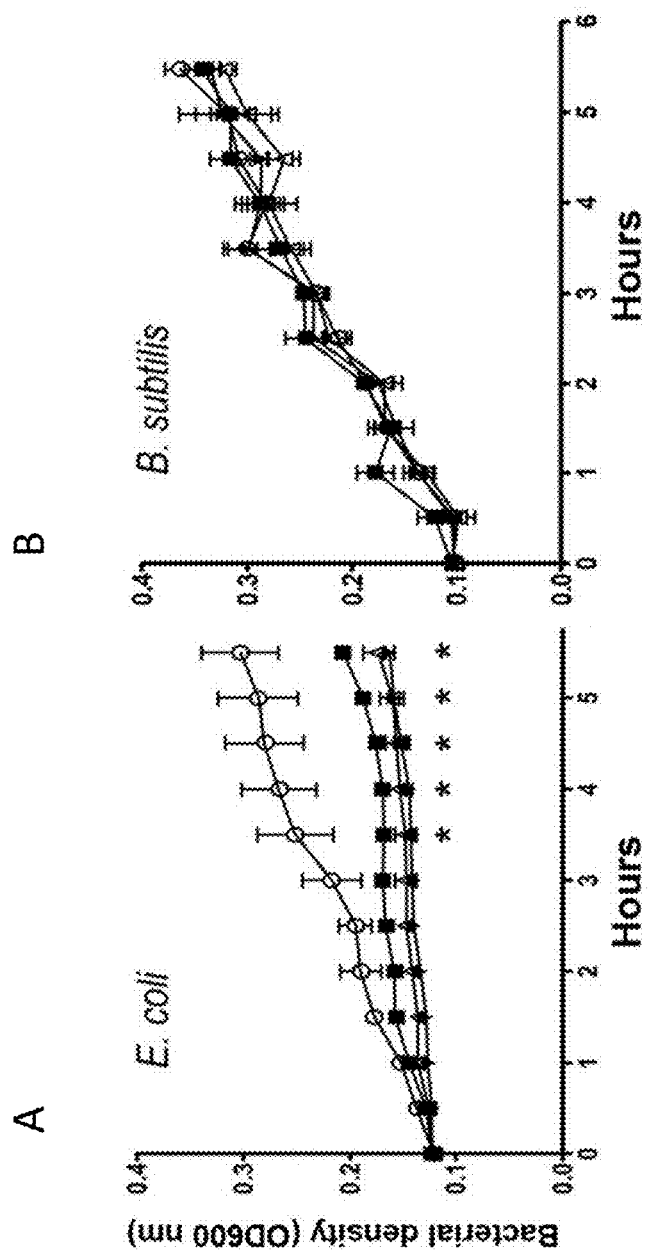
FIG. 3 illustrates growth inhibition of *E. coli* by rASS or PEGylated-rASS.
Figure 3C:
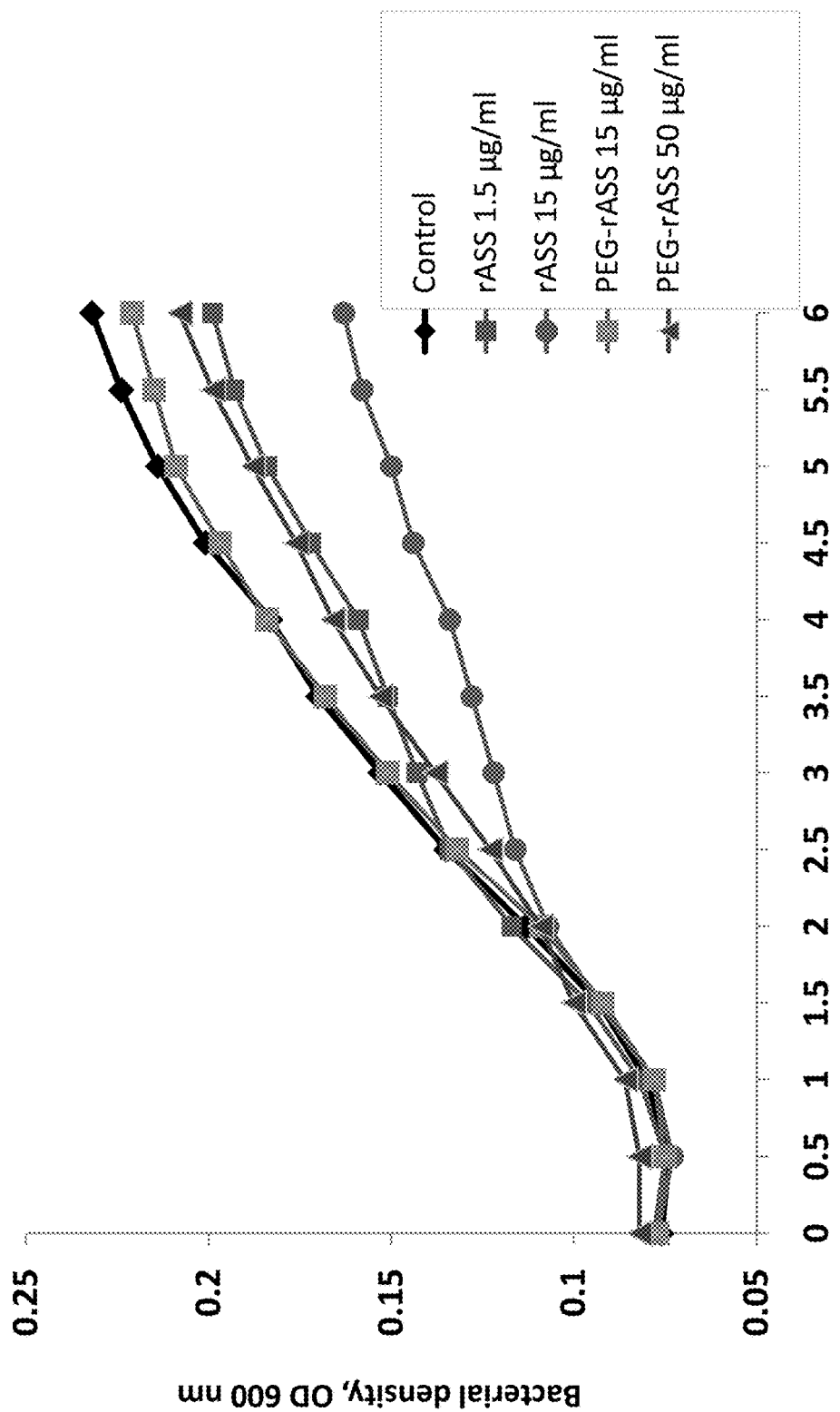

A strong physical interaction of ASS with LPS could be responsible for a deposition of de novo synthesized rASS into inclusion bodies in bacteria at 37° C. The inhibitory effect of rASS or PEGylated-rASS on E. coli or B. subtilis bacterial growth is assessed as optical density at 600 nm at different concentrations of rASS. E. coli (K-12 strain) expressing LPS on cell surface or B. subtilis (control) are allowed to grow in the absence or presence of rASS or PEGylated-rASS (0.25 or 0.5 µg/ml) in a 96-well plate in LB (Luria-Bertani) medium (Novagen) with a starting density of 0.06 optical units (at 600 nm). After each hour up to 6 hours, OD at 600 nm is measured to determine bacterial growth rate. FIG. 3 shows that 3 to 6 hours following addition to suspension cultures, 50 µg/ml of rASS (FIG. 3A) or PEGylated rASS (FIG. 3C) significantly suppresses E. coli growth demonstrating direct antibacterial effects of the rASS supplement. rASS and PEGylated-rASS similarly inhibit growth. rASS shows no apparent reduction in growth of B. subtilis. (FIG. 3B)

Example 4

Western Blot Analyses

For western blot analyses samples are homogenized on ice in western blot buffer. The samples are subjected to SDS-polyacrylamide gel electrophoresis (SDS-PAGE) and electroblotted onto polyvinylidene difluoride membranes. Membranes are blocked in 10 mM Tris, pH 7.5, 100 mM NaCl, and 0.1% Tween-20 containing 5% nonfat dry milk for 60 min at room temperature. After overnight incubation with primary antibodies, proteins are detected either using secondary antibody conjugated to horseradish peroxidase (HRP) and a chemiluminescence detection system, or secondary antibody conjugated to alkaline phosphatase (ALP) and colorimetric detection system.

Example 5

Attenuation of LPS Toxicity by rASS in Macrophage Cell Cultures

The beneficial effects of rASS against LPS toxicity are examined on mammalian cells in culture using release of lactate dehydrogenase (LDH) into the medium as an indicator of LPS toxicity.

RAW 264.7 mouse macrophages are purchased from American Type Culture Collection (Manassas, Va.) and cultured in DMEM supplemented with 10% fetal bovine serum and antibiotic-antimycotic solution (100 U/ml penicillin, 100 µg/ml streptomycin and 25 µg/ml amphotericin B) in 5% $CO_2$ at 37° C. Cultures are passaged every 3 to 5 days, and cells are detached by brief trypsin treatment and visualized in an inverted microscope.

The macrophages are treated with LPS (0.1-1 µg/ml), rASS (1 and 10 µg/ml) and anti-LPS core antibodies (0.1 µg/ml). At different time points cell-conditioned media from each well is saved for LDH release assay. Cells at the terminal time points (6 or 18 h) are washed and subjected to MTS assay. The cells are lysed for western blot analyses of αII-spectrin breakdown products.

Figure 4:
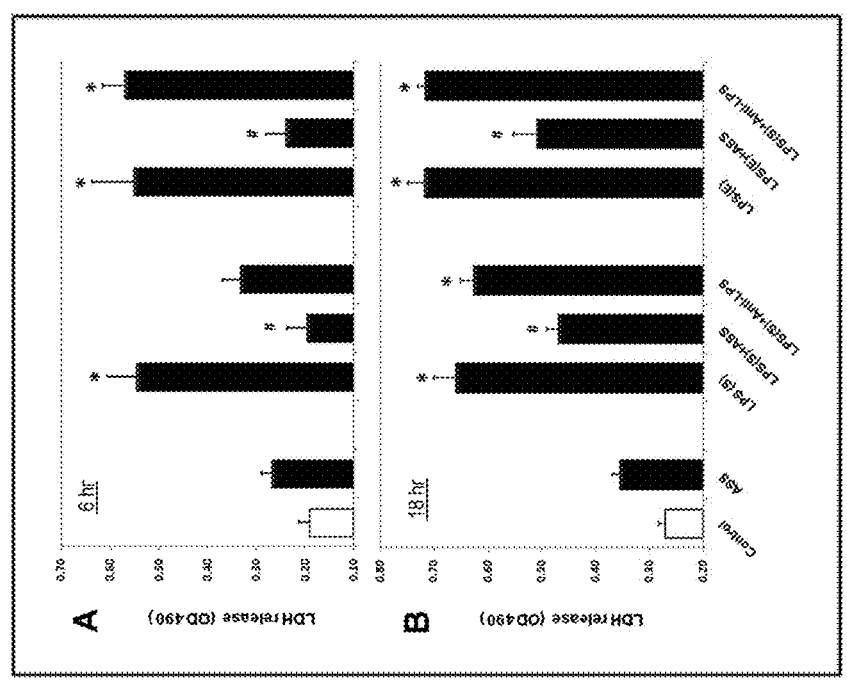
FIG. 4 illustrates attenuation of LPS toxicity by rASS in macrophage cell cultures.

At 1 µg/ml, LPS from both E. coli, LPS(E) or S. enterica, LPS(S) exhibit a remarkable cytotoxicity as indicated by a sharp increase of medium LDH levels at 6 and 18 hours following LPS challenge (FIGS. 4A and 4B). Pre-incubation of LPS with rASS (1 µg/ml) for 1 hour before addition significantly reduces the LDH release by two types of LPS at 6 and 18 hours after treatment (FIGS. 4A and 4B). In contrast, pre-incubation of LPS with anti-LPS antibody (0.1 µg/ml) decreases LDH release induced by LPS(S) at 6 hours and does not affect LPS(E) toxicity or LPS(S) effects 18 hours following addition (FIGS. 4A and 4B). Thus, cell injury induced by LPS from either E. coli or S. enterica can be mitigated by rASS presence in growth media even more consistently than by anti-LPS antibodies. The protective action of rASS is significant at both time points studied (6 and 18 hours).

Example 6

LDH Release and MTS Mitochondrial Function Assays

CytoTox 96® Cytotoxicity Assay (Promega, Madison, Wis.) is used to quantitatively measure lactate dehydrogenase (LDH) release to assess the relative number of lysed cells according to the manufacturer's instructions. CellTiter 96 AQ Assay (Promega) is used to quantitatively measure the conversion of a tetrazolium compound, MTS, into a formazan product by the mitochondria of living cells to assess the relative cell viability according to the manufacturer's instructions.

Figure 5:
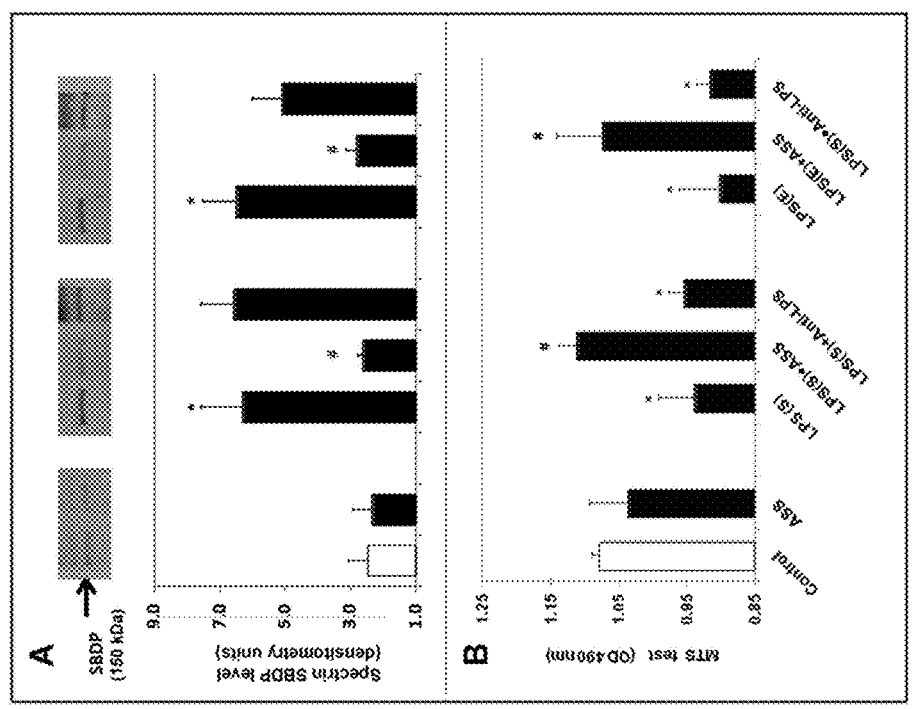
FIG. 5 illustrates decreases in LPS induced cellular cytotoxicity by rASS as measured by reduction in breakdown in cytoskeletal αII-spectrin (A) or in an MTS reduction assay (B)
Figure 6:
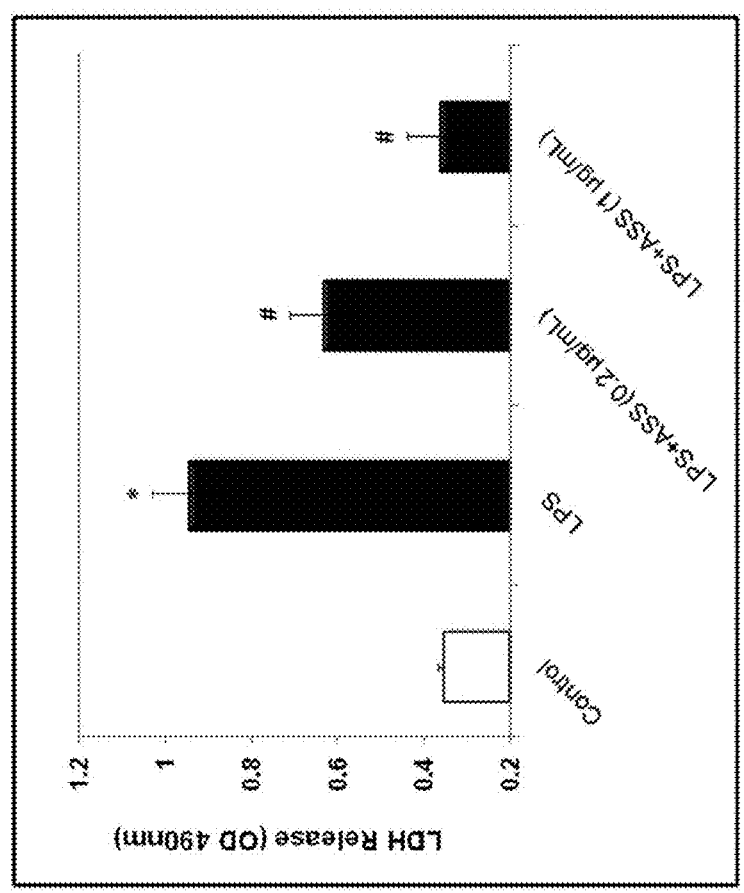
FIG. 6 illustrates reduction in LPS-induced cytotoxicity in a rASS dose-dependent fashion.

Cytotoxicity and cell death in many tissues involve caspase-3 and calpain-2 activation that results in a cleavage of several common proteins such as major cytoskeletal αII-spectrin. In RAW264.7 cells, both LPS types at 1 μ/ml induce αII-spectrin breakdown and generation of a 150 kDa fragment (SBDP150) within 18 hours after treatment (FIG. 5A), while pretreatment with rASS (1 μg/ml) significantly attenuates LPS-induced SBDP150 formation. The LDH release and αII-spectrin breakdown in response to LPS are accompanied by a decrease in cell viability as indicated by a mitochondrial respiration activity of cultured macrophages measured using an MTS reduction assay. Pre-incubation with rASS protects the cells and increases cell viability at 18 hours following treatment with LPS (FIG. 5B). In contrast, LPS-induced cell damage assessed by MTS test is not affected by anti-LPS antibody (0.1 μg/ml) (FIG. 5B). Complete blocking of mitochondrial dysfunction caused by both LPS (E) and LPS(S) is achieved at the rASS:LPS mass ratio of about 1:1. Finally, rASS is capable of mitigating endotoxin-induced cellular damage when added after LPS. As shown in FIG. 6, addition of rASS 1 hour after LPS nearly abolishes LPS-induced cytotoxicity in a rASS dose-dependent fashion in mouse macrophages.

Example 7

ELISA Analyses

ASS SW ELISA Assay. The levels of endogenous ASS in serum is determined by SW ELISA assay (Banyan Biomarkers, Inc.) using polyclonal ASS antibody as capture and mouse monoclonal as detection antibody. Color development is accomplished using anti-mouse HRP-conjugated Abs followed by TMB substrate incubation. ASS levels are calculated from a calibration curve using human rASS or PEGylated-rASS prepared as above as an ASS standard.

Quantitative detection of TNF-α and CRP in animal blood serum was performed, using sandwich ELISA kits from eBioscience Inc. and BioVendor LLC respectively, according to the manufacturer's instructions.

Example 8

LPS and ASS Complex Formation

The rASS preparations are examined for LPS binding affinity by gel-shift assay of rASS-LPS complex formation. Purified LPS (*E. coli*), LPS (*S. enterica*), and rASS alone or in combination are incubated for 1 hour at 37° C., then subjected to non-denaturing gel electrophoresis, run with 192 mM Tris, 325 mM glycine, (pH 8.3) at 25 mA for 2.5 hours using 4-20% gradient polyacrylamide (PAA) gels (Invitrogen, Carlsbad, Calif.) in a tray filled with ice-water slurry. Gels are first pre-run with same buffer for 15 min. rASS is visualized in the gel by Coomassie Blue as a single band, while LPS alone is not detected (FIG. 2D). In contrast, this technique reveals the pre-incubated rASS-LPS complexes as heterogeneous patches with a dramatic mobility shift compared to rASS alone (FIG. 2D) and similar to LPS visualized by silver staining.

Example 9

Beneficial Effects of rASS in Rodent Models of Endotoxic Shock

Figure 7:
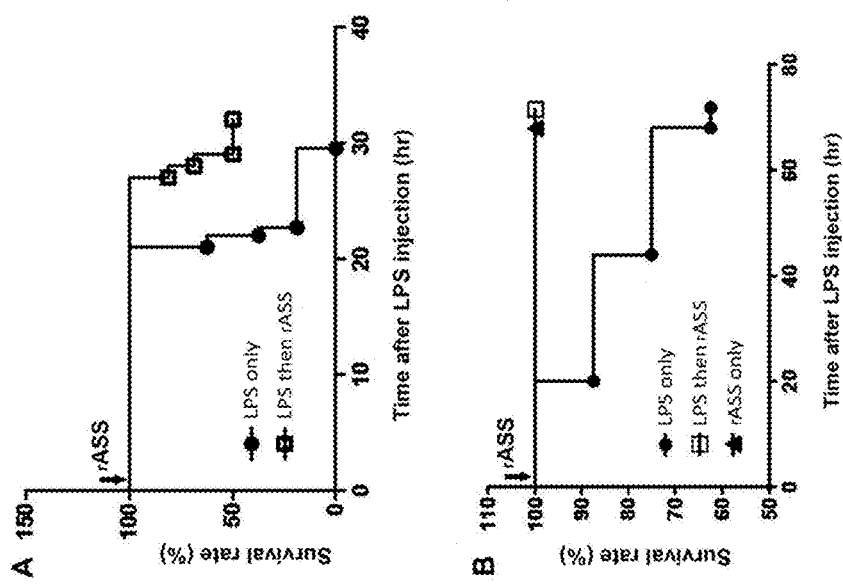
FIG. 7 illustrates beneficial effects of rASS treatment on mouse (A) and rat (B) survival after challenge with LPS.

A model of experimental endotoxemia in Balb/c mice is used to characterize the efficacy of rASS in protecting an immunologically intact host against serious LPS attack. Groups of 6 mice receive intra-peritoneal (i.p.) injections of saline with either 15 mg/kg *E. coli* LPS or 15 mg/kg *S. enterica* LPS followed in 1 hr by infusion with 5 mg/kg rASS. Survival is recorded during a period of 32 hr. As shown in FIG. 7A, LPS mice have 80% mortality at 24 hr and all die by 30 hr. In contrast, 50% mice challenged by LPS and subsequently treated once with rASS at 3:1 mass ratio survive at 32 hr (FIG. 7A).

For survival experiments, Sprague-Dawley rats are randomly divided into three groups (at least 4 in each group). Group 1 receives an i.p. injection 5 mg/kg rASS, group 2 is given 25 mg/kg *E. coli* LPS followed in 1 hr by infusion with 5 mg/kg rASS, and group 3 is given 25 mg/kg *E. coli* LPS alone. Survival is recorded during a period of 72 hr.

In rat endotoxemia model, a bolus injection of LPS (25 mg/kg, i.p.) results in a 72-hr survival of 60% (FIG. 7B). In contrast, 100% rats survive when rASS is injected 1 hour following LPS challenge at rASS/LPS mass ratio of 1:5 (FIG. 7B).

Example 10

Effects of rASS on the Release of Endotoxic Shock-related Markers

To assess endotoxin-induced systemic inflammation and organ injury, several common serum markers are assessed. For these biomarker release studies, rats are given i.p. either *E. coli* LPS (25 mg/kg or 5 mg/kg) alone, or LPS preincubated (1 hr, 37° C.) with rASS (5 mg/kg), or LPS followed in 1 hr by infusion with rASS. TNF-α, LDH and CRP levels are assessed in sera prepared from rat blood samples 3 hr (TNF-α detection) or 72 hr (LDH and CRP detection) after LPS injection.

Example 11

Figure 8:
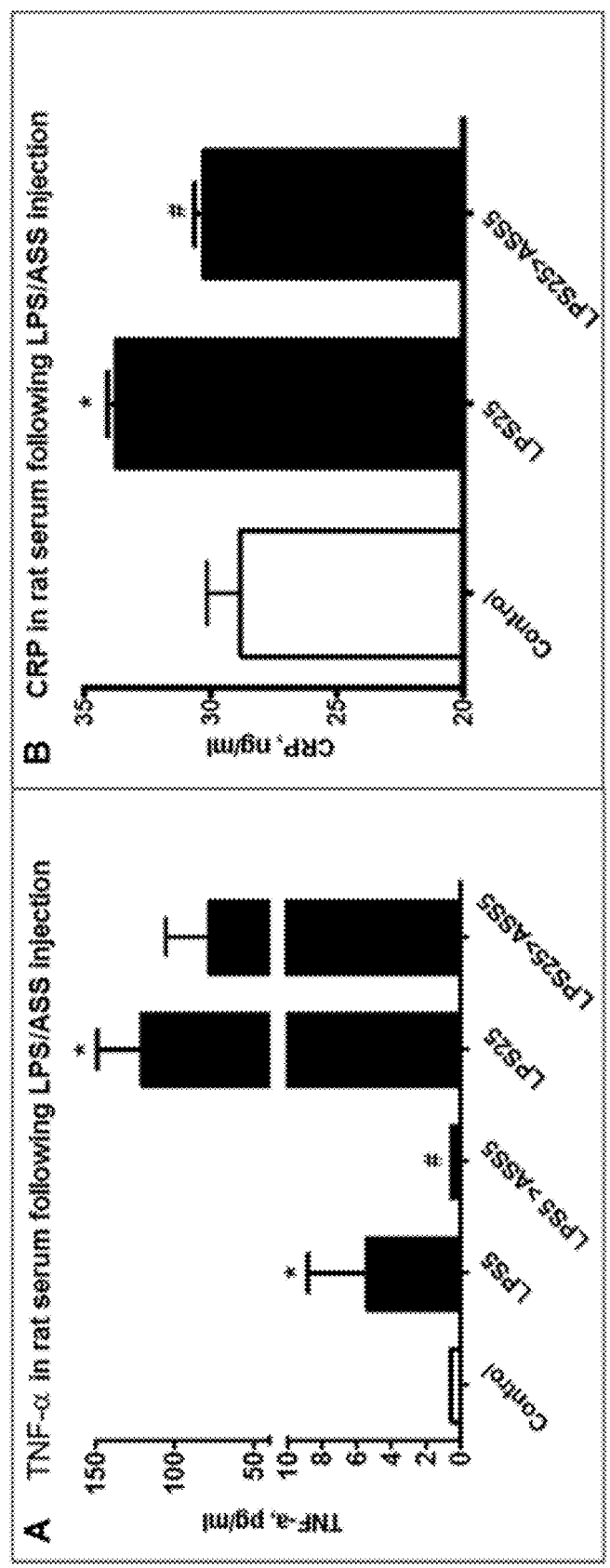
FIG. 8 illustrates suppression of TNF-α release (A) and C-reactive protein (B) levels by rASS in rat endotoxemia.

Suppression of TNF-α Release and C-reactive Protein (CRP) Levels by rASS in Rat Endotoxemia To determine whether the protective activity of ASS is associated with pro-inflammatory cytokine attenuation in vivo we measure the serum TNF-α level in endotoxemic rats challenged as in Example 10. As shown in FIG. 8A, LPS injected at 25 mg/kg induces TNF-α rise in serum up to about 125 pg/ml at 3 hours post injection, while administration of 5 mg/kg of rASS one hour after LPS decreases TNF-α production by 40% (FIG. 8A). Moreover, lower magnitude increases of TNF-α induced by i.p. treatment with 5 mg/kg LPS are abrogated by a subsequent injection of 5 mg/kg of rASS (FIG. 8A).

Concomitant increase in serum CRP levels are abolished by rASS injected 1 hr following sub-lethal 25 mg/kg LPS challenge thus returning CRP to control levels (FIG. 8B).

Example 12

Inhibition of Serum LDH Release in Endotoxemia Rats

Figure 9:
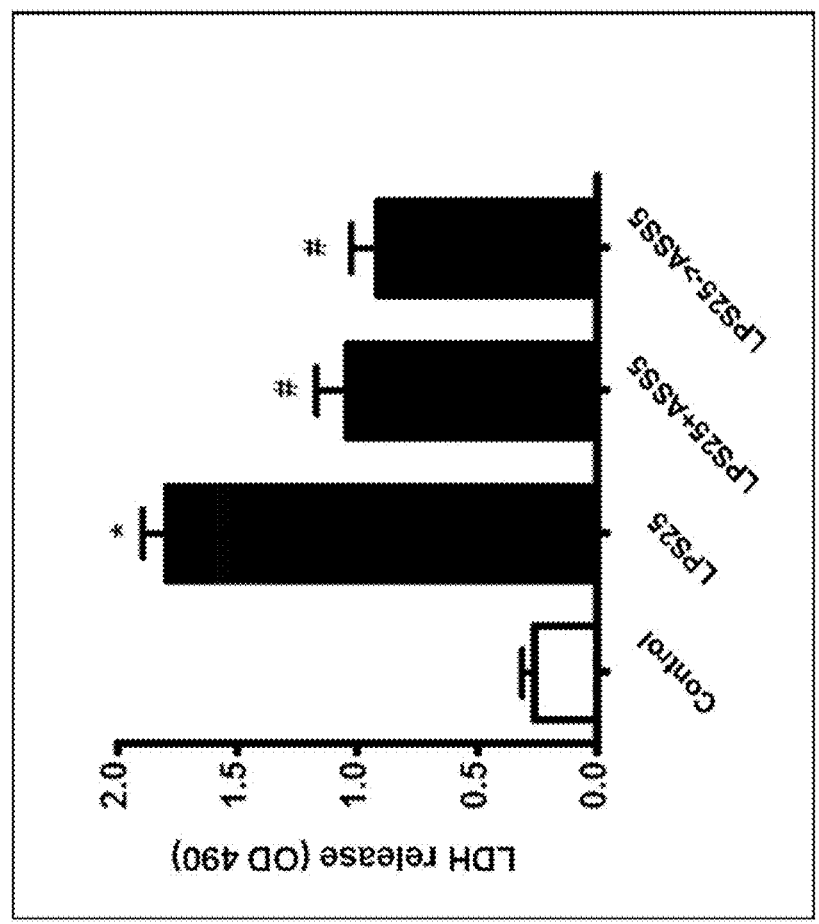
FIG. 9 illustrates inhibition of serum LDH release in subjects by simultaneous or sequential administration of rASS.

Lactate dehydrogenase (LDH) is a cytosolic enzyme present in many body tissues, including the liver. Thus, elevated serum levels of LDH indicate a leakage of LDH from tissues, potentially due to a multi-organ damage elicited by various insults. FIG. 9 shows that LPS administered to rats at the sub-lethal dose of 25 mg/kg induces nearly 7-fold increase of LDH in serum compared with control. However, when the LPS challenge is accompanied or followed by i.p. injection of 5 mg/kg of rASS, the LDH release is reduced by correspondingly 45% and 49%. (FIG. 9).

Example 13

ASS PEGylation Increases rASS Enzymatic Activity rASS is either used alone or is PEGylated as described in Example 2. A PEGylated-rASS and rASS enzymatic activity test is developed according to the principle enzymatic reaction catalyzed by ASS followed by determination of inorganic phosphate produced by pyrophosphatase (Schema 1).

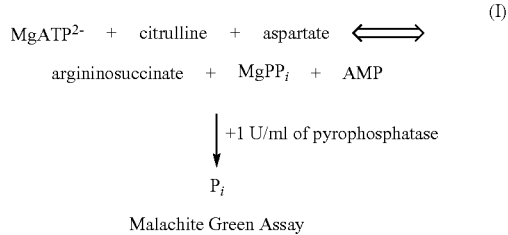

Malachite Green Assay

Briefly, 5 µl of sample is added to 45 µl of 10 mM Tris-HCl (pH 7.5) containing 6 mM $MgCl_2$, 20 mM KCl, 1 mM ATP, and 1 U/ml of pyrophosphatase plus or minus substrates of 1 mM aspartic acid and 12.5 mM citrulline in a 96-well microtiter plate. Inorganic phosphate (Pi) generated in the reaction is determined using malachite green assay kit using the manufacturer's instructions (RND Systems, Minneapolis, Minn.).

Figure 10:
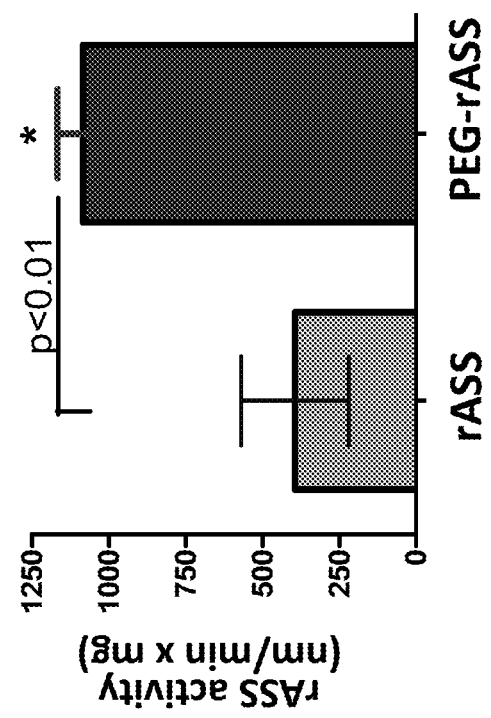
FIG. 10 illustrates the nearly 3-fold higher activity of PEGylated-rASS/mg protein vs. non-PEGylated rASS.

FIG. 10 illustrates greater than 2.5-fold increased in vitro enzymatic activity of PEGylated rASS relative to rASS alone (p<0.01) unexpectedly indicating that PEGylation improves the in vitro enzymatic activity of rASS.

Example 14

ASS PEGylation Increases rASS in vivo Stability

The stability of PEGylated-rASS is studied and compared to that of rASS alone. 5 mg/kg rASS and PEGylated rASS are injected intraperitoneal (i.p.) in adult male Sprague-Dawley rats (200-225 g) (Harlan Laboratories Inc., Indianapolis, Ind.) housed under constant temperature (22° C.) and humidity with 12 hours light/dark cycle with access to chow and water ad libitum. Blood is collected from heart of anesthetized animals 3 h and 20 h after injection, using at least 3 rats for each time point. The level of rASS or PEGylated-rASS is determined by SW-ELISA as described in Example 7.

Figure 11:
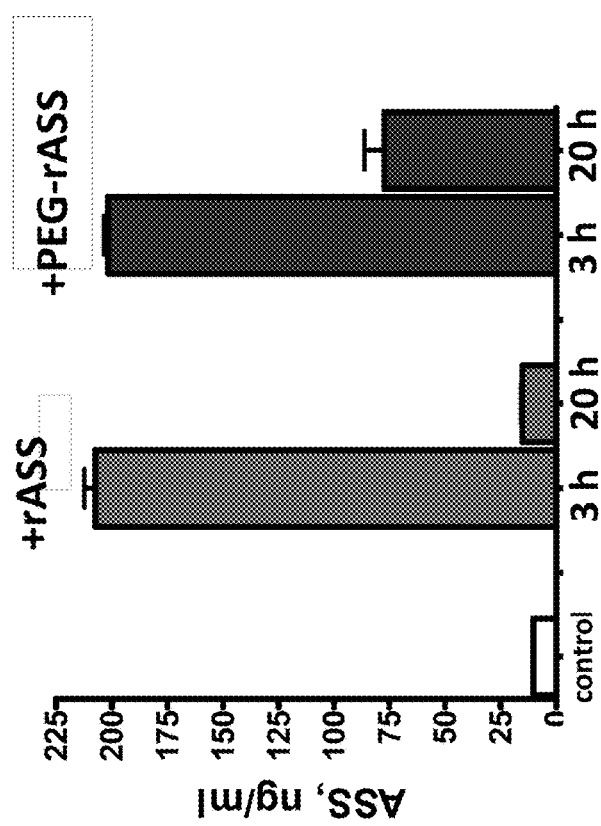
FIG. 11 illustrates that PEGylated-rASS is significantly more stable, and is retained in circulation for a much longer time after i.p. injection into subjects vs. non-PEGylated rASS.

As illustrated in FIG. 11, PEG-rASS is significantly more stable, and is retained in circulation for a much longer time after i.p. injection vs. non-PEGylated rASS. These results combined with the increased enzymatic activity of PEGylated-rASS indicated that PEGylation produces a more robust rASS molecule with overall unexpectedly greater ability to bind and clear LPS from a pathogenic Gram-negative bacteria infected subject.

Statistics

Statistical analyses are performed using GraphPad Prism 5 software. Data are evaluated by 2-tailed unpaired t-test. The criterion for statistical significance is set at p<0.05 or p<0.01.

Sequences

SEQ ID No. 1: *Homo sapiens* argininosuccinate synthetase 1 (ASS) protein (412 aa):
MSSKGSVVLAYSGGLDTSCILVWLKEQGYDVIAYLANIGQKEDFEEARK
KALKLGAKKVFIEDVSREFVEEFIWPAIQSSALYEDRYLLGTSLARPCI
ARKQVEIAQREGAKYVSHGATGKGNDQVRFELSCYSLAPQIKVIAPWRM
PEFYNRFKGRNDLMEYAKQHGIPIPVTPKNPWSMDENLMHISYEAGILE
NPKNQAPPGLYTKTQDPAKAPNTPDILEIEFKKGVPVKVTNVKDGTTHQ
TSLELFMYLNEVAGKHGVGRIDIVENRFIGMKSRGIYETPAGTILYHAH
LDIEAFTMDREVRKIKQGLGLKFAELVYTGFWHSPECEFVRHCIAKSQE
RVEGKVQVSVLKGQVYILGRESPLSLYNEELVSMNVQGDYEPTDATGFI
NINSLRLKEYHRLQSKVTAK
(SEQ ID NO. 1)

SEQ ID No. 2: *Homo sapiens* argininosuccinate synthetase 1 (ASS) cDNA (1239 nt):
ATGTCCAGCAAAGGCTCCGTGGTTCTGGCCTACAGTGGCGGCCTGGACA
CCTCGTGCATCCTCGTGTGGCTGAAGGAACAAGGCTATGACGTCATTGC
CTATCTGGCCAACATTGGCCAGAAGGAAGACTTCGAGGAAGCCAGGAAG
AAGGCACTGAAGCTTGGGGCCAAAAAGGTGTTCATTGAGGATGTCAGCA
GGGAGTTTGTGGAGGAGTTCATCTGGCCGGCCATCCAGTCCAGCGCACT
GTATGAGGACCGCTACCTCCTGGGCACCTCTCTTGCCAGGCCCTGCATC
GCCCGCAAACAAGTGGAAATCGCCCAGCGGGAGGGGGCCAAGTATGTGT
CCCACGGCGCCACAGGAAAGGGGAACGATCAGGTCCGGTTTGAGCTCAG
CTGCTACTCACTGGCCCCCCAGATAAAGGTCATTGCTCCCTGGAGGATG
CCTGAATTCTACAACCGGTTCAAGGGCCGCAATGACCTGATGGAGTACG
CAAAGCAACACGGGATTCCCATCCCGGTCACTCCCAAGAACCCGTGGAG
CATGGATGAGAACCTCATGCACATCAGCTACGAGGCTGGAATCCTGGAG
AACCCCAAGAACCAAGCGGCTCCAGGTCTCTACACGAAGACCCAGGACC
CAGCCAAAGCCCCCAACACCCCTGACATTCTCGAGATCGAGTTCAAAAA
AGGGGTCCCTGTGAAGGTGACCAACGTCAAGGATGGCACCACCCACCAG
ACCTCCTTGGAGCTCTTCATGTACCTGAACGAAGTCGCGGGCAAGCATG
GCGTGGGCCGTATTGACATCGTGGAGAACCGCTTCATTGGAATGAAGTC
CCGAGGTATCTACGAGACCCCAGCAGGCACCATCCTTTACCATGCTCAT
TTAGACATCGAGGCCTTCACCATGGACCGGGAAGTGCGCAAAATCAAAC
AAGGCCTGGGCTTGAAATTTGCTGAGCTGGTGTATACCGGTTTCTGGCA
CAGCCCTGAGTGTGAATTTGTCCGCCACTGCATCGCCAAGTCCCAGGAG
CGAGTGGAAGGGAAAGTGCAGGTGTCCGTCCTCAAGGGCCAGGTGTACA
TCCTCGGCCGGGAGTCCCCACTGTCTCTCTACAATGAGGAGCTGGTGAG
CATGAACGTCCAGGGTGATTATGAGCCAACTGATGCCACCGGGTTCATC
AACATCAATTCCCTCAGGCTGAAGGAATATCATCGTCTCCAGAGCAAGG
TCACTGCCAAATAG
(SEQ ID NO. 2)

It is appreciated that all reagents are obtainable by sources known in the art unless otherwise specified. Methods of nucleotide amplification, cell transfection, and protein expression and purification are within the level of skill in the art.

Any patents or publications mentioned in this specification are incorporated herein by reference to the same extent as if each individual publication is specifically and individually indicated to be incorporated by reference for the material for which each reference is cited as well all other material taught therein.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The foregoing description is illustrative of particular embodiments of the invention, but is not meant to be a limitation upon the practice thereof. The following claims, including all equivalents thereof, are intended to define the scope of the invention.

The invention claimed is:

1. A process of treating bacterial endotoxin exposure in a subject, comprising:
   obtaining a sample from the subject exposed to a bacterial endotoxin circulating in blood of the subject prior to said obtaining;
   detecting whether argininosuccinate synthetase is present in the biological sample by contacting the biological sample with an anti-argininosuccinate synthetase antibody and detecting binding between the argininosuccinate synthetase and the antibody;
   determining that levels and activity of the argininosuccinate synthetase in said sample from the subject are elevated over a normal level and normal activity of the arginosuccinate synthetase absent exposure to the bacterial endotoxin; and
   administering a therapeutically effective amount of additional argininosuccinate synthetase to the subject when the argininosuccinate synthetase in the biological sample is detected over the normal level and the normal activity.

2. The process of claim 1 wherein said sample comprises serum.

3. The process of claim 1 wherein said subject is infected with a pathogenic Gram-negative bacteria as a source of said bacterial endotoxin.

4. The process of claim 1 wherein the argininosuccinate synthetase has an amino acid sequence of SEQ ID NO: 1.

5. The process of claim 1 wherein said argininosuccinate synthetase protein has an amino acid sequence of a truncation of SEQ ID NO: 1 retaining a binding site for said bacterial endotoxin.

6. The process of claim 1 wherein said subject is human.

7. The process of claim 1 wherein said argininosuccinate synthetase is recombinantly expressed.

8. The process of claim 1 wherein said argininosuccinate synthetase is PEGylated.

9. The process of claim 1 wherein said argininosuccinate synthetase is PEGylated with a PEG comprising $PEG_{12}$.

10. The process of claim 1 wherein said argininosuccinate synthetase is PEGylated with an unbranched PEG, a branched PEG, or combinations thereof.

11. The process of claim 10 wherein said argininosuccinate synthetase and said PEG are present in a ratio ranging from 1:1 to 1:400.

12. The process of claim 1 wherein said subject is infected with a pathogenic Gram-negative bacteria.

* * * * *

SEQUENCE LISTING

```
<160> NUMBER OF SEQ ID NOS: 4

<210> SEQ ID NO 1
<211> LENGTH: 412
<212> TYPE: PRT
<213> ORGANISM: Homo sapiens

<400> SEQUENCE: 1

Met Ser Ser Lys Gly Ser Val Val Leu Ala Tyr Ser Gly Gly Leu Asp
1               5                   10                  15

Thr Ser Cys Ile Leu Val Trp Leu Lys Glu Gln Gly Tyr Asp Val Ile
            20                  25                  30

Ala Tyr Leu Ala Asn Ile Gly Gln Lys Glu Asp Phe Glu Glu Ala Arg
        35                  40                  45

Lys Lys Ala Leu Lys Leu Gly Ala Lys Lys Val Phe Ile Glu Asp Val
    50                  55                  60

Ser Arg Glu Phe Val Glu Glu Phe Ile Trp Pro Ala Ile Gln Ser Ser
65                  70                  75                  80

Ala Leu Tyr Glu Asp Arg Tyr Leu Leu Gly Thr Ser Leu Ala Arg Pro
                85                  90                  95

Cys Ile Ala Arg Lys Gln Val Glu Ile Ala Gln Arg Glu Gly Ala Lys
            100                 105                 110

Tyr Val Ser His Gly Ala Thr Gly Lys Gly Asn Asp Gln Val Arg Phe
        115                 120                 125

Glu Leu Ser Cys Tyr Ser Leu Ala Pro Gln Ile Lys Val Ile Ala Pro
    130                 135                 140

Trp Arg Met Pro Glu Phe Tyr Asn Arg Phe Lys Gly Arg Asn Asp Leu
145                 150                 155                 160

Met Glu Tyr Ala Lys Gln His Gly Ile Pro Ile Pro Val Thr Pro Lys
                165                 170                 175

Asn Pro Trp Ser Met Asp Glu Asn Leu Met His Ile Ser Tyr Glu Ala
            180                 185                 190

Gly Ile Leu Glu Asn Pro Lys Asn Gln Ala Pro Pro Gly Leu Tyr Thr
        195                 200                 205

Lys Thr Gln Asp Pro Ala Lys Ala Pro Asn Thr Pro Asp Ile Leu Glu
    210                 215                 220

Ile Glu Phe Lys Lys Gly Val Pro Val Lys Val Thr Asn Val Lys Asp
225                 230                 235                 240

Gly Thr Thr His Gln Thr Ser Leu Glu Leu Phe Met Tyr Leu Asn Glu
                245                 250                 255

Val Ala Gly Lys His Gly Val Gly Arg Ile Asp Ile Val Glu Asn Arg
            260                 265                 270

Phe Ile Gly Met Lys Ser Arg Gly Ile Tyr Glu Thr Pro Ala Gly Thr
        275                 280                 285

Ile Leu Tyr His Ala His Leu Asp Ile Glu Ala Phe Thr Met Asp Arg
    290                 295                 300
```

```
Glu Val Arg Lys Ile Lys Gln Gly Leu Gly Leu Lys Phe Ala Glu Leu
305                 310                 315                 320

Val Tyr Thr Gly Phe Trp His Ser Pro Glu Cys Glu Phe Val Arg His
                325                 330                 335

Cys Ile Ala Lys Ser Gln Glu Arg Val Glu Gly Lys Val Gln Val Ser
            340                 345                 350

Val Leu Lys Gly Gln Val Tyr Ile Leu Gly Arg Glu Ser Pro Leu Ser
        355                 360                 365

Leu Tyr Asn Glu Glu Leu Val Ser Met Asn Val Gln Gly Asp Tyr Glu
    370                 375                 380

Pro Thr Asp Ala Thr Gly Phe Ile Asn Ile Asn Ser Leu Arg Leu Lys
385                 390                 395                 400

Glu Tyr His Arg Leu Gln Ser Lys Val Thr Ala Lys
                405                 410

<210> SEQ ID NO 2
<211> LENGTH: 1239
<212> TYPE: DNA
<213> ORGANISM: Homo sapiens

<400> SEQUENCE: 2
atgtccagca aaggctccgt ggttctggcc tacagtggcg gcctggacac ctcgtgcatc      60
ctcgtgtggc tgaaggaaca aggctatgac gtcattgcct atctggccaa cattggccag     120
aaggaagact tcgaggaagc caggaagaag gcactgaagc ttggggccaa aaaggtgttc     180
attgaggatg tcagcaggga gtttgtggag gagttcatct ggccggccat ccagtccagc     240
gcactgtatg aggaccgcta cctcctgggc acctctcttg ccaggccctg catcgcccgc     300
aaacaagtgg aaatcgccca gcggggagggg gccaagtatg tgtcccacgg cgccacagga     360
aaggggaacg atcaggtccg gtttgagctc agctgctact cactggcccc ccagataaag     420
gtcattgctc cctggaggat gcctgaattc tacaaccggt tcaagggccg caatgacctg     480
atggagtacg caaagcaaca cgggattccc atcccggtca ctcccaagaa cccgtggagc     540
atggatgaga acctcatgca catcagctac gaggctggaa tcctggagaa ccccaagaac     600
caagcgcctc caggtctcta cacgaagacc caggacccag ccaaagcccc caacacccct     660
gacattctcg agatcgagtt caaaaaaggg gtccctgtga aggtgaccaa cgtcaaggat     720
ggcaccaccc accagacctc cttggagctc ttcatgtacc tgaacgaagt cgcgggcaag     780
catggcgtgg gccgtattga catcgtggag aaccgcttca ttggaatgaa gtcccgaggt     840
atctacgaga ccccagcagg caccatcctt taccatgctc atttagacat cgaggccttc     900
accatggacc gggaagtgcg caaaatcaaa caaggcctgg gcttgaaatt tgctgagctg     960
gtgtataccg gtttctggca cagccctgag tgtgaatttg tccgccactg catcgccaag    1020
tcccaggagc gagtggaagg gaaagtgcag gtgtccgtcc tcaagggcca ggtgtacatc    1080
ctcggccggg agtccccact gtctctctac aatgaggagc tggtgagcat gaacgtgcag    1140
ggtgattatg agccaactga tgccaccggg ttcatcaaca tcaattccct caggctgaag    1200
gaatatcatc gtctccagag caaggtcact gccaaatag                           1239

<210> SEQ ID NO 3
<211> LENGTH: 32
<212> TYPE: DNA
<213> ORGANISM: Artificial Sequence
<220> FEATURE:
<223> OTHER INFORMATION: Synthetic
```

```
<400> SEQUENCE: 3
atgtccagca aaggctccgt ggttctggcc ta                                    32

<210> SEQ ID NO 4
<211> LENGTH: 50
<212> TYPE: DNA
<213> ORGANISM: Artificial Sequence
<220> FEATURE:
<223> OTHER INFORMATION: Synthetic

<400> SEQUENCE: 4
tataaagctt tcaatggtga tggtgatgat gtttggcagt gaccttgctc                 50
```